United States Patent
Kim et al.

(10) Patent No.: US 8,192,956 B2
(45) Date of Patent: Jun. 5, 2012

(54) HYBRID GENES AND ENZYMES OF GLUCANASE AND DEXTRANSUCRASE AND PROCESSES FOR PREPARING ISOMALTO-OLIGOSACCHARIDES OR DEXTRAN USING THE SAME

(75) Inventors: Do Man Kim, Gwang-ju (KR); Mi Young Seo, Jeollanamdo (KR)

(73) Assignee: Industry Foundation of Chonnam National University, Gwang-Ju (KR)

( * ) Notice: Subject to any disclaimer, the term of this patent is extended or adjusted under 35 U.S.C. 154(b) by 1082 days.

(21) Appl. No.: 12/063,678

(22) PCT Filed: Apr. 28, 2007

(86) PCT No.: PCT/KR2007/002106
§ 371 (c)(1),
(2), (4) Date: Feb. 12, 2008

(87) PCT Pub. No.: WO2007/126278
PCT Pub. Date: Nov. 8, 2007

(65) Prior Publication Data
US 2011/0129879 A1    Jun. 2, 2011

(30) Foreign Application Priority Data

Apr. 28, 2006  (KR) .................. 10-2006-0038710

(51) Int. Cl.
*C12P 21/04* (2006.01)
*C12P 21/06* (2006.01)
*C12P 19/18* (2006.01)
*C12N 9/10* (2006.01)
*C12N 1/20* (2006.01)
*C12N 15/70* (2006.01)
*C07H 21/04* (2006.01)

(52) U.S. Cl. ........ 435/69.7; 435/69.1; 435/97; 435/193; 435/320.1; 435/252.3; 536/23.2

(58) Field of Classification Search .................. None
See application file for complete search history.

(56) References Cited

U.S. PATENT DOCUMENTS 4,861,381 A     8/1989  Paul et al.
5,585,545 A  *  12/1996 Bennett et al. ................ 800/267

FOREIGN PATENT DOCUMENTS

| KR | 10-2002-0017869 A | 3/2002 |
| KR | 10-2004-0092250 A | 11/2004 |
| KR | 10-2005-0059425 A | 6/2005 |

OTHER PUBLICATIONS

Kim, D. and Day, D. F. (1994). A new process for the production of clinical dextran by mixed-culture fermentation of *Lipomyces starkeyi* and *Leuconostoc mesenteroides*. *Enzyme and Microbial Technology*, 16(10): 844-848.

* cited by examiner

*Primary Examiner* — Anand Desai
*Assistant Examiner* — Iqbal H Chowdhury
(74) *Attorney, Agent, or Firm* — Saliwanchik, Lloyd & Eisenschenk

(57) ABSTRACT

Disclosed are hybrid genes of glucanase and dextransucrase, recombinant vectors comprising said hybrid genes, microorganisms which are transformed with said recombinant vectors, hybrid enzymes which are expressed from said hybrid genes, and processes for preparing isomalto-oligosaccharides or dextran using said microorganisms or enzymes. Expensive isomalto-oligosaccharides and low molecular weight dextran for clinical use can be produced simply and effectively from cheap substrate-sucrose, using a single bacterial strain or enzyme.

21 Claims, 15 Drawing Sheets

SEQ. ID. NO: 1

ATGAAGCATTACCTCCGTCTATTGGCCTCAGCATTTGCGCTGCTGCTCCTGCT
GCCGGCTGCCGGCCAGGAGCCAGCCGCTGCGACAGAACAGACCGGTTTCACTG
CCACCGGACCCGGCCTTCGGACCTGGTGGCACAACAACTACGAATACAACCCA
ACCTCACCCACCCAGAACGGCACAGTCCGCCGGTCATCCTTTTACGAGGTGCA
AGTAGCCACAGCAACGGCACCAGGAACGCGCTACGACTCCTTCGCCTACATGA
GCATTCCCCGCAGCGGAAAGGGGAAGACCGGCTACACGGAGCCGGACGGAGCA
GAGTTCTCTTCGTCAGCGAACCTCTCAATGAGCTGGTCCAGCTTTGAGTACTC
AACGGACGTCTGGGTGGACGTCAAACTCACGACAGGCCAAACAATCACGTCTG
TGGATCAGGTAACGATCCGGCCCAGCAAGTACACCTTCGAGAAAGAGCTGGTG
AACCCCAGCACCATCCGGGTCAAAGTCCCCTACTCGTCGACGGGCTACCGGCT
CTCAGTGGAATTCGCGCCCAGCTCTTCACTGCATACAACGACATGTCCGGAA
CGGCGGGGGTGTTGACTGAAACCGGTGGCGGGGATCACCGCGCCATCCATACC
GAACCACGGAATTCCATGATGATCTTCGCCGAGCCGACCCTGGGCGGCGGCGA
GGCGGAGCGGTTGATTCCCACCTCCGCATCCGGAGCTATCAACTATCCGCAGG
AAGGCCTGGTCGACAACCTGGGGTCGGTCACCGAGGAGATCATCTACTTCCGG
CCCGGGACGTATTACATGGATCGGACCACCGGGCCTCGATGCCGCCCAACGT
CAAATGGATCTACCTGGCTCCCGGGGCGTATGTCAAAGGTGCCTTCTACTTCC
CCAACTCGACGCAGGGCGTCTACAAGGTCACTGGCCGCGGCGTGCTCTCCGGC
GAACAGTACGTCTATGAAGCCGATACAACCACCAGCGGGTACACGCATTCAAC
CGGCGCTAATTGCCACAACACCTGCGTGAAGATGCTGGAATTCACGTCTTCAT
CGACCATGCAGCAGTACTTGGACGTGGAGGGAATCACCATCAGCGAACCTCCC
TACCACTCCTTTGTCATTTACGGGCCGCAAAACGCCTATGAGATGGAAATGCG
GGTGGATAACTACAAGCAGGTGGGCAGCTGGTACTGGCAGACCGACGGGATGG
AACTCTACGAGGGCGGGCGGATGAACAACACCTTTTTCCACTCCAATGATGAC
GTCCTGAAGCTCTACCACAGCAACGTGACGGTGGATAACACGGTGATCTGGAA
GAACGAGAACGGTCCGGTCATCCAGTGGGGTTGGGCGCCGTACAACATTGACA
ATGTGGTCGTCACCAACACAGACGTCATCCACAACCGCATGTATTGGAAGGAC
GTCAAATACAACACCTGCATCATCAACTCGTCCTCCACTACGCGGACATGGG
CTCCTCCACCACGGCGAACCCCGCCACCACGATCAGGAATTTCCGGCTGGAGA
ACATTACTGTCGAAGGAATGACCAACTGCGCCCTCAGGATCTATGCGCTTTCC
AACACCGAGAACATCCACATCAAGAAGCTGAATATCGGAAGCTGGAACGGGTT
GGACCACACGTCCCAGGTGAGCCACCTGAAGCGCTATTCAGACACTGCCAACA
ACAAGGTCTGGCTGGGCAACGAGACTGTCGACAGCAGAGGCATCAAGCTCGAG

FIG. 3

SEQ. ID. NO: 1 (cont.)

```
AACTACACCGTCGGCGGGGCCAGGATCGACAAAACCACGACCAACTGGAGCGA
TAACCAGGCGGGCCGTCTCGGCTTCGACGGCGAAAACTGGGATAACTGGAACG
CGTGGAGATCTATGCTGTCTATGACCGCTACTTCACAAAATGTTAATGCAGAT
AGCACAAACACAGTGACGGATAAGTCAGTTACTGTCTCCAATAATTCGAATAC
AACCAATCAACACGATACTGTCGTTGACAAACAAACGATACCTGTCAAAAATG
ACCAAACAACACAACAAATCGCCGCAAATGCCACCCAAGCAGAAAAAGTAAAA
GCATCAGACACAACGACTGATACGGAAAAGCAAGCTGAAACGGCAAACAACAC
TAACAAGGATTCGATAGATAATCTCACCAAGCAGTTGCCGGCTGTTACACCAA
CAGCTAATCAAAAAACTGGTTATCTGGAAAAAGATGGTAAATGGTACTATGT
AACCAGTGATAACACACTTGCTAAGGGGTTGACTACTGTTGACAACCACAAGC
AGTATTTTGACAACAATGGCGTGCAGGCAAAAGGCCAATTCGTTACCGATAAC
AGTAAAACATACTATCTCGATCCTAACTCCGGTAACGCAGTAACCGGGATACA
ACAAATTGGCTCACAAACATTAGCCTTCAATGACAACGGTGAACAAGTTTTTG
CTGATTTCTATACAGCGCCAGATGGCAAAACTTATTATTTTGACGATAAAGG
ACAAGCAACTATTGGTCTAAAGGCCATTAATGGGCACAATTATTACTTCGATA
GTTTGGGACAACTAAAAAAAGGATTTACCGGTGTCATTGACGGTCAAGTACG
CTATTTTGATCAAGAATCAGGACAAGAGGTATCAACAACCGACTCACAAATCA
AAGAAGGTTTAACTTCTCAGACAACAGACTATACAGCACATAATGCCGTTCAC
AGCACCGATAGCGCTGATTTCGACAATTTTAATGGTTATTTGACCGCTTCTTC
ATGGTATCGCCCTAAAGATGTTTTAAGAAATGGTCAACACTGGGAAGCAACAA
CAGCTAATGACTTCCGGCCCATTGTGTCAGTTTGGTGGCCTAGCAAGCAAACA
CAAGTAAATTACCTAAACTACATGTCTCAAATGGGACTCATTGACAATCGTCA
GATGTTCTCGCTAAAAGACAATCAAGCCATGTTGAATATTGCTTGCACAACAG
TCCAACAAGCAATTGAAACAAAAATCGGTGTGGCTAATAGTACAGCATGGCTT
AAAACAGCCATTGATGATTTCATTCGTACACAGCCACAATGGAACATGTCGAG
TGAAGATCCCAAAAATGATCATTTACAAAACGGCGCTTTGACTTTCGTCAACA
GTCCATTGACACCAGATACTAACTCTAATTTCAGACTATTAAATCGCACACCA
ACAAACCAGACAGGTGTGCCAAAATATACAATTGATCAATCTAAGGGTGGTT
TTGAACTCTTACTCGCTAATGATGTAGACAACTCTAATCCTGTTGTGCAAGCT
GAGCAGTTAAATTGGTTACACTATTTGATGAATTTTGGTAGCATTACAGCAA
ACGATTCTGCTGCTAATTTTGATGGGATACGTGTCGATGCTGTCGATAATGT
TGACGCTGATTTACTCCAGATTGCAGCAGATTATTTCAAAGCTGCTTATGGT
GTTGATAAAAATGACGCAACAGCAAATCAACATCTTTCAATTCTTGAAGATT
GGAGCCATAACGACCCTGAATACGTGAAGGATTTTGGTAATAATCAACTCACA
ATGGATGATTACATGCATACCCAGTTAATCTGGTCCTTGACTAAAGATATGC
```

FIG. 4

SEQ. ID. NO: 1 (cont.)

```
AACTACACCGTCGGCGGGGCCAGGATCGACAAAACCACGACCAACTGGAGCGA
TAACCAGGCGGGCCGTCTCGGCTTCGACGGCGAAAACTGGGATAACTGGAACG
CGTGGAGATCTATGCTGTCTATGACGGCTAGTTCACAAAATGTTAATGCAGAT
AGCACAAACACAGTGACGGATAAGTCAGTTACTGTCTCCAATAATTCGAATAC
AACCAATCAACACGATACTGTCGTTGACAAACAAACGATACCTGTCAAAAATG
ACCAAACAACACAACAAATCGCCGCAAATGCCACCCAAGCAGAAAAAGTAAAA
GCATCAGACACAACGACTGATACGCAAAAGCAAGCTGAAACGGCAAACAACAC
TAACAAGGATTCGATAGATAATCTCACCAAGCAGTTGCCGGCTGTTACACCAA
CAGCTAATCAAAAAACTGGTTATCTGGAAAAGATGGTAAATGGTACTATGT
AACCAGTGATAACACACTTGCTAAGGGGTTGACTACTGTTGACAACCACAAGC
AGTATTTTGACAACAATGGCGTGCAGGCAAAAGGCCAATTCGTTACCGATAAC
AGTAAAACATACTATCTCGATCCTAACTCCGGTAACGCAGTAACCGGGATAGA
ACAAATTGGCTCACAAACATTAGCCTTCAATGACAACGGTGAACAAGTTTTTG
CTGATTTCTATACAGCGCCAGATGGCAAAACTTATTATTTTGACGATAAAGG
ACAAGCAACTATTGGTCTAAAGGCCATTAATGGGCACAATTATTACTTCGATA
GTTTGGGACAACTAAAAAAAGGATTTACCGGTGTCATTGACGGTCAAGTACG
CTATTTTGATCAAGAATCAGGACAAGAGGTATCAACAACCGACTCACAAATCA
AAGAAGGTTTAACTTCTCAGACAACAGACTATACAGCACATAATGCCGTTCAC
AGCACCGATAGCGCTGATTTCGACAATTTTAATGGTTATTTGACCGCTTCTTC
ATGGTATCGCCCTAAAGATGTTTTAAGAAATGGTCAACACTGGGAAGCAACAA
CAGCTAATGACTTCCGGCCCATTGTGTCAGTTTGGTGGCCTAGCAAGCAAACA
CAAGTAAATTACCTAAACTACATGTCTCAAATGGGACTCATTGACAATCGTCA
GATGTTCTCGCTAAAAGACAATCAAGCCATGTTGAATATTGCTTGCACAACAG
TCCAACAAGCAATTGAAACAAAAATCGGTGTGGCTAATAGTACAGCATGGCTT
AAAACAGCCATTGATGATTTCATTCGTACACAGCCACAATGGAACATGTCGAG
TGAAGATCCCAAAAATGATCATTTACAAAACGGCGCTTTGACTTTCGTCAACA
GTCCATTGACACCAGATACTAACTCTAATTTCAGACTATTAAATCGCACACCA
ACAAACCAGACAGGTGTGCCAAAATATACAATTGATCAATCTAAGGGTGGTT
TTGAACTCTTACTCGCTAATGATGTAGACAACTCTAATCCTGTTGTGCAAGCT
GAGCAGTTAAATTGGTTACACTATTTGATGAATTTTGGTAGCATTACAGCAA
ACGATTCTGCTGCTAATTTTGATGGGATACGTGTCGATGCTGTCGATAATGT
TGACGCTGATTTACTCCAGATTGCAGCAGATTATTTCAAAGCTGCTTATGGT
GTTGATAAAAATGACGCAACAGCAAATCAACATCTTTCAATTCTTGAAGATT
GGAGCCATAACGACCCTGAATACGTGAAGGATTTTGGTAATAATCAACTCACA
ATGGATGATTACATGCATACCCAGTTAATCTGGTCCTTGACTAAAGATATGC
```

FIG. 5

SEQ. ID. NO: 1 (cont.)

AAGGGCGTCAAGTATTTAATCAATACATTACTGACCAAACCGGTACCGCCTAT
TACTTCCAGAATGATGGCACAATGGTCACTTCTGGCTTCACTGAAATCGATGG
TCATAAGCAATACTTCTACAAGAACGGCACACAAGTCAAAGGGCAATTTGTAT
CAGACACTGATGGTCACGTTTTCTACTTAGAAGCTGGTAACGGCAACGTGGCG
ACACAAGATTTGCACAAAATAGTCAAGGTCAGTGGTTCTATTTGGGTAATG
ATGGCATTGCCTTGACTGGTTTGCAAACAATCAATGGTGTTCAAAATTATTT
CTACGCCGATGGTCATCAAAGTAAGGGTGATTTTATTACGATACAAAATCACG
TATTATATACTAACCCACTAACTGGCGCTATAACGACAGGTATGCAACAAATT
GGTGACAAGATTTTTGTCTTTGACAATACGGGCAACATGTTGACCAATCAAT
ACTATCAAACACTAGATGGCCAATGGTTACATTTAAGCACTCAAGGTCCAGCA
GACACTGGTTTGGTAAACATTAATGGTAATTTGAAATATTTCCAAGCTAATG
GTCGGCAAGTGAAAGGTCAATTTGTGACTGATCCTATCACGAACGTGAGTTA
TTATATGAATGCCACTGATGGTTCGGCAGTATTTAATGACTACTTTACCTAT
CAAGGCCAATGGTATTTAACGGATAGTAATTATCAACTCGTCAAAGGATTTA
AAGTTGTTAATAATAAGCTACAACATTTTGATGAAATAACAGGCGTACAAAC
TAAATCAGCTCATATCATCGTTAATAATCGAACATACATTTTCGATGACCAAG
GTTACTTTGTCTCAGTCGCTTAA

FIG. 6

SEQ. ID. NO: 2

ATGCTGTCTATGACCGCTACTTCACAAAATGTTAATGCAGATAGCACAAACAC
AGTGACGGATAAGTCAGTTACTGTCTCCAATAATTCGAATACAACCAATCAAC
ACGATACTGTCGTTGACAAACAAACGATACCTGTCAAAAATGACCAAACAACA
CAACAAATCGCCGCAAATGCCACCCAAGCAGAAAAAGTAAAAGCATCAGACAC
AACGACTGATACGCAAAAGCAAGCTGAAACGGCAAACAACACTAACAAGGATT
CGATAGATAATCTCACCAAGCAGTTGCCGGCTGTTACACCAACAGCTAATCAA
AAAACTGGTTATCTGGAAAAAGATGGTAAATGGTACTATGTAACCAGTGATA
ACACACTTGCTAAGGGGTTGACTACTGTTGACAACCACAAGCAGTATTTTGAC
AACAATGGCGTGCAGGCAAAAGGCCAATTCGTTACCGATAACAGTAAAACATA
CTATCTCGATCCTAACTCCGGTAACGCAGTAACCGGGATACAACAAATTGGCT
CACAAACATTAGCCTTCAATGACAACGGTGAACAAGTTTTTGCTGATTTCTAT
ACAGCGCCAGATGGCAAAACTTATTATTTTGACGATAAAGGACAAGCAACTAT
TGGTCTAAAGGCCATTAATGGGCACAATTATTACTTCGATAGTTTGGGACAA
CTAAAAAAAGGATTTACCGGTGTCATTGACGGTCAAGTACGCTATTTTGATC
AAGAATCAGGACAAGAGGTATCAACAACCGACTCACAAATCAAAGAAGGTTTA
ACTTCTCAGACAACAGACTATACAGCACATAATGCCGTTCACAGCACCGATAG
CGCTGATTTCGACAATTTTAATGGTTATTTGACCGCTTCTTCATGGTATCGC
CCTAAAGATGTTTTAAGAAATGGTCAACACTGGGAAGCAACAACAGCTAATGA
CTTCCGGCCCATTGTGTCAGTTTGGTGGCCTAGCAAGCAAACACAAGTAAATT
ACCTAAACTACATGTCTCAAATGGACTCATTGACAATCGTCAGATGTTCTCG
CTAAAAGACAATCAAGCCATGTTGAATATTGCTTGCACAACAGTCCAACAAGC
AATTGAAACAAAAATCGGTGTGGCTAATAGTACAGCATGGCTTAAAACAGCCA
TTGATGATTTCATTCGTACACAGCCACAATGGAACATGTCGAGTGAAGATCCC
AAAAATGATCATTTACAAAACGGCGCTTTGACTTTCGTCAACAGTCCATTGAC
ACCAGATACTAACTCTAATTTCAGACTATTAAATCGCACACCAACAAACCAGA
CAGGTGTGCCAAAATATACAATTGATCAATCTAAGGGTGGTTTTGAACTCTT
ACTCGCTAATGATGTAGACAACTCTAATCCTGTTGTGCAAGCTGAGCAGTTAA
ATTGGTTACACTATTTGATGAATTTTGGTAGCATTACAGCAAACGATTCTGC
TGCTAATTTTGATGGGATACGTGTCGATGCTGTCGATAATGTTGACGCTGAT
TTACTCCAGATTGCAGCAGATTATTTCAAAGCTGCTTATGGTGTTGATAAAA
ATGACGCAACAGCAAATCAACATCTTTCAATTCTTGAAGATTGGAGCCATAAC
GACCCTGAATACGTGAAGGATTTTGGTAATAATCAACTCACAATGGATGATT
ACATGCATACCCAGTTAATCTGGTCCTTGACTAAAGATATGCGTATGCGTGGT

FIG. 7

SEQ. ID. NO: 2 (cont.)

ACCATGCAACGCTTCATGGACTATTACCTCGTCAATCGCAATCACGATAGTAC
CGAAAACACTGCCATTCCAAATTACAGCTTTGTTCGCGCACACGATAGTGAAG
TACAAACAGTCATTGCTCAAATTATTTCTGAGTTACATCCCGACGTAAAAAAT
AGTTTGGCACCAACAGCAGACCAGCTAGCCGAAGCCTTTAAAATTTATAATAA
CGATGAAAAACAGGCGGATAAGAAATATACACAATACAACATGCCTAGCGCCT
ATGCGATGCTGTTAACTAATAAAGATACAGTACCGCGCGTTTATTATGGTGA
TTTATACACCGATGATGGTCAATATATGGCAAATAAGTCCCTTATTTTGAT
GCCATCAACGGCTTGCTAAAGTCACGTATCAAATATGTTGCTGGTGGTCAGTC
AATGGCTGTTGATCAAAACGATATCCTGACAAATGTTCGTTATGGTAAAGGT
GCCATGAGTGTGACAGATAGCGGTAATGCAGACACACGAACACAAGGTATTGG
TGTGATTGTCAGTAATAAAGAAAATCTGGCCTTAAAATCAGGCGACACGGTG
ACATTACACATGGGTGCCGCTCACAAAAATCAAGCATTCAGATTATTATTAGG
GACAACTGCTGACAATTTGTCTTATTATGATAATGACAACGCCCCAGTAAAGT
ACACCAATGATCAGGGCGATTTAATTTTTGATAATACTGAAATCTATGGTGT
CCGTAACCCGCAAGTCTCTGGCTTCTTAGCTGTTTGGGTGCCTGTTGGGGCTG
ACAGCCATCAAGACGCGCGTACTTTGTCTGACGACACAGCCCATCATGATGGC
AAAACCTTCCACTCAAATGCTGCTTTAGATTCTCAGGTTATTTACGAAGGTT
TTTCAAATTTCCAAGCTTTTGCCACAAACACTGAAGACTATACAAATGCTGTC
ATTGCAAAAAATGGTCAGTTATTCAAAGATTGGGGTATCACAAGTTTCCAGT
TGGCACCACAATATCGTTCAAGCACCGATACCAGTTTCTTAGATTCAATTATC
CAAAATGGTTATGCCTTTACAGATCGTTATGATTTAGGCTACGGTACACCAAC
AAAATATGGCACAGTTGACCAGTTACGCGATGCCATCAAGGCTCTGCACGCAA
ATGGCATCCAAGCAATCGCTGACTGGGTACCCGACCAAATTTATAATTTACCG
GGTCAAGAATTAGCGACCGTCAGCCGAACAAACTCTTATGGTGATAAAGACAC
TAACTCAGATATTGATCAGTCACTATATGTCATACAAAGTCGTGGTGGTGGT
AAATACCAAGCACAGTATGGCGGTGCCTTCTTATCCGATATCCAGAAAAAATA
TCCAGCACTTTTCGAAACAAAACAAATTTCTACAGGGCTACCTATGGATCCTA
GTCAGAAAATAACAGAATGGTCTGGTAAATACTTTAATGGCTCAAATATTCA
AGGCAAAGGGGCTGGCTATGTCTTGAAAGACAGTGGTACCGATCAATACTAT
AAGGTTACATCAAACAATAATAATCGTGACTTCTTGCCAAAACAATTAACAGA
TGACTTATCTGAAACCGGATTTGTCCGCGATAACATTGGTATGGTCTATTAC
ACACTGAGTGGCTATCTAGCTCGAAACACCTTTATACAAGATGATAATGGCAA
TTATTATTACTTTGATAGCACCGGCCATCTCGTTACTGGCTTCCAGAATATTA
ATAACCATCACTATTTCTTCCTACCAAACGGTATTGAACTCGTTCAATCTTTC
TTACAGAATGCTGACGGTTCAACGATTTATTTTGACCAAAAAGGGCGTCAAG

FIG. 8

SEQ. ID. NO: 2 (cont.)

ACCATGCAACGCTTCATGGACTATTACCTCGTCAATCGCAATCACGATAGTAC
CGAAAACACTGCCATTCCAAATTACAGCTTTGTTCGCGCACACGATAGTGAAG
TACAAACAGTCATTGCTCAAATTATTTCTGAGTTACATCCCGACGTAAAAAAT
AGTTTGGCACCAACAGCAGACCAGCTAGCCGAAGCCTTTAAAATTTATAATAA
CGATGAAAACAGGCGGATAAGAAATATACACAATACAACATGCCTAGCGCCT
ATGCGATGCTGTTAACTAATAAAGATACAGTACCGCGCGTTTATTATGGTGA
TTTATACACCGATGATGGTCAATATATGGCAAATAAGTCCCCTTATTTTGAT
GCCATCAACGGCTTGCTAAAGTCACGTATCAAATATGTTGCTGGTGGTCAGTC
AATGGCTGTTGATCAAAACGATATCCTGACAAATGTTCGTTATGGTAAAGGT
GCCATGAGTGTGACAGATAGCGGTAATGCAGACACACGAACACAAGGTATTGG
TGTGATTGTCAGTAATAAAGAAAATCTGGCCTTAAAATCAGGCGACACGGTG
ACATTACACATGGGTGCCGCTCACAAAAATCAAGCATTCAGATTATTATTAGG
GACAACTGCTGACAATTTGTCTTATTATGATAATGACAACGCCCAGTAAAGT
ACACCAATGATCAGGGCGATTTAATTTTTGATAATACTGAAATCTATGGTGT
CCGTAACCCGCAAGTCTCTGGCTTCTTAGCTGTTTGGGTGCCTGTTGGGGCTG
ACAGCCATCAAGACGCGCGTACTTTGTCTGACGACACAGCCCATCATGATGGC
AAAACCTTCCACTCAAATGCTGCTTTAGATTCTCAGGTTATTTACGAAGGTT
TTTCAAATTTCCAAGCTTTTGCCACAAACACTGAAGACTATACAAATGCTGTC
ATTGCAAAAAATGGTCAGTTATTCAAAGATTGGGGTATCACAAGTTTCCAGT
TGGCACCACAATATCGTTCAAGCACCGATACCAGTTTCTTAGATTCAATTATC
CAAAATGGTTATGCCTTTACAGATCGTTATGATTTAGGCTACGGTACAGCAAC
AAAATATGGCACAGTTGACCAGTTACGCGATGCCATCAAGGCTCTGCACGCAA
ATGGCATCCAAGCAATCGCTGACTGGGTACCCGACCAAATTTATAATTTACCG
GGTCAAGAATTAGCGACCGTCACCCGAACAAACTCTTATGGTGATAAAGACAC
TAACTCAGATATTGATCAGTCACTATATGTCATACAAAGTCGTGGTGGTGGT
AAATACCAAGCACAGTATGGCGGTGCCTTCTTATCCGATATCCAGAAAAAATA
TCCAGCACTTTTCGAAACAAAACAAATTTCTACAGGGCTACCTATGGATCCTA
GTCAGAAAATAACAGAATGGTCTGGTAAATACTTTAATGGCTCAAATATTCA
AGGCAAAGGGGCTGGCTATGTCTTGAAAGACAGTGGTACCGATCAATACTAT
AAGGTTACATCAAACAATAATAATCGTGACTTCTTGCCAAAACAATTAACAGA
TGACTTATCTGAAACCGGATTTGTCCGCGATAACATTGGTATGGTCTATTAC
ACACTGAGTGGCTATCTAGCTCGAAACACCTTTATACAAGATGATAATGGCAA
TTATTATTACTTTGATAGCACCGGCCATCTCGTTACTGGCTTCCAGAATATTA
ATAACCATCACTATTTCTTCCTACCAAACGGTATTGAACTCGTTCAATCTTTC
TTACAGAATGCTGACGGTTCAACGATTTATTTTGACCAAAAAGGGCGTCAAG

FIG. 9

SEQ. ID. NO: 2 (cont.)

CAACCGGCGCTAATTGCCACAACACCTGCGTGAAGATGCTGGAATTCACGTCT
TCATCGACCATGCAGCAGTACTTGGACGTGGAGGGAATCACCATCAGCGAACC
TCCCTACCACTCCTTTGTCATTTACGGGCCGCAAAACGCCTATGAGATGGAAA
TGCGGGTGGATAACTACAAGCAGGTGGGCAGCTGGTACTGGCAGACCGACGGG
ATGGAACTCTACGAGGGCGGGCGGATGAACAACACCTTTTTCCACTCCAATGA
TGACGTCCTGAAGCTCTACCACAGCAACGTGACGGTGGATAACACGGTGATCT
GGAAGAACGAGAACGGTCCGGTCATCCAGTGGGGTTGGGCGCCGTACAACATT
GACAATGTGGTCGTCACCAACACAGACGTCATCCACAACCGCATGTATTGGAA
GGACGTCAAATACAACACCTGCATCATCAACTCGTGCTCCCACTACGCGGACA
TGGGCTCCTCCACCACGGCGAACCCCGCCACCACGATCAGGAATTTCCGGCTG
GAGAACATTACTGTCGAAGGAATGACCAACTGCGCCCTCAGGATCTATGCGCT
TTCCAACACCGAGAACATCCACATCAAGAACCTGAATATCGGAAGCTGGAACG
GGTTGGACCACACGTCCCAGGTGAGCCACCTGAAGCGCTATTCAGACACTGCC
AACAACAAGGTCTGGCTGGGCAACGAGACTGTCGACAGCAGAGGCATCAAGCT
CGAGAACTACACCGTCGGCGGGGCCAGGATCGACAAAACCACGACCAACTGGA
GCGATAACCAGGCGGGCCGTCTCGGCTTCGACGGCGAAAACTGGATAACTGG
AACGCGTGGTGA

[Figure 12]
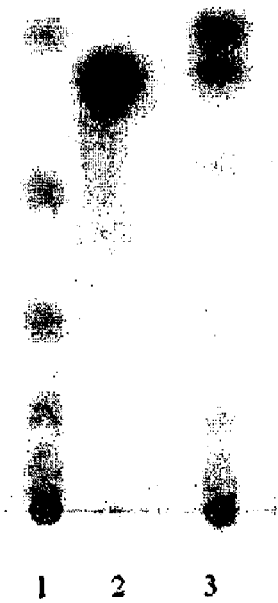
1  2  3
[Figure 13]
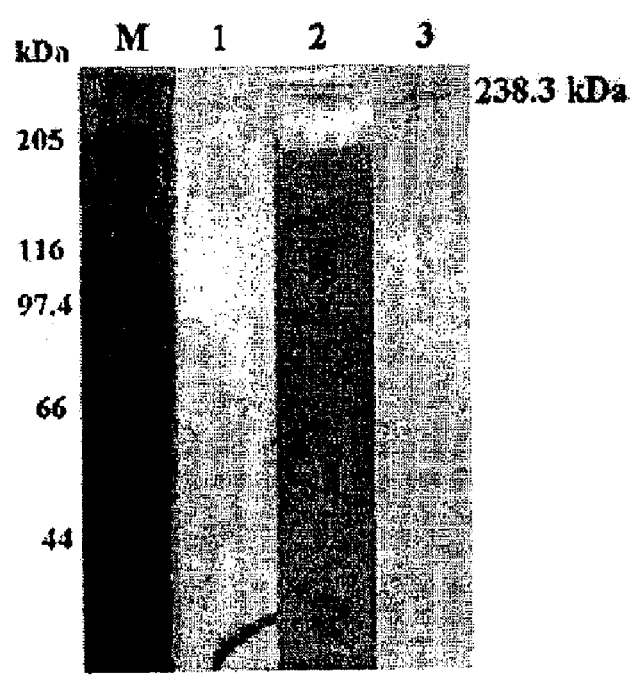

[Figure 14]
| Sucrose | 342 | 2.534 | 13.616 |
|---|---|---|---|
| T-10 | 10000 | 4.000 | 10.55 |
| T-40 | 40000 | 4.602 | 8.617 |
| T-70 | 70000 | 4.845 | 8.158 |
| peak 1 | 69455.6 | 4.842 | 8.202 |
| peak 2 | 1668.4 | 3.222 | 12.092 |
| peak 3 | 73.3 | 1.865 | 15.352 |
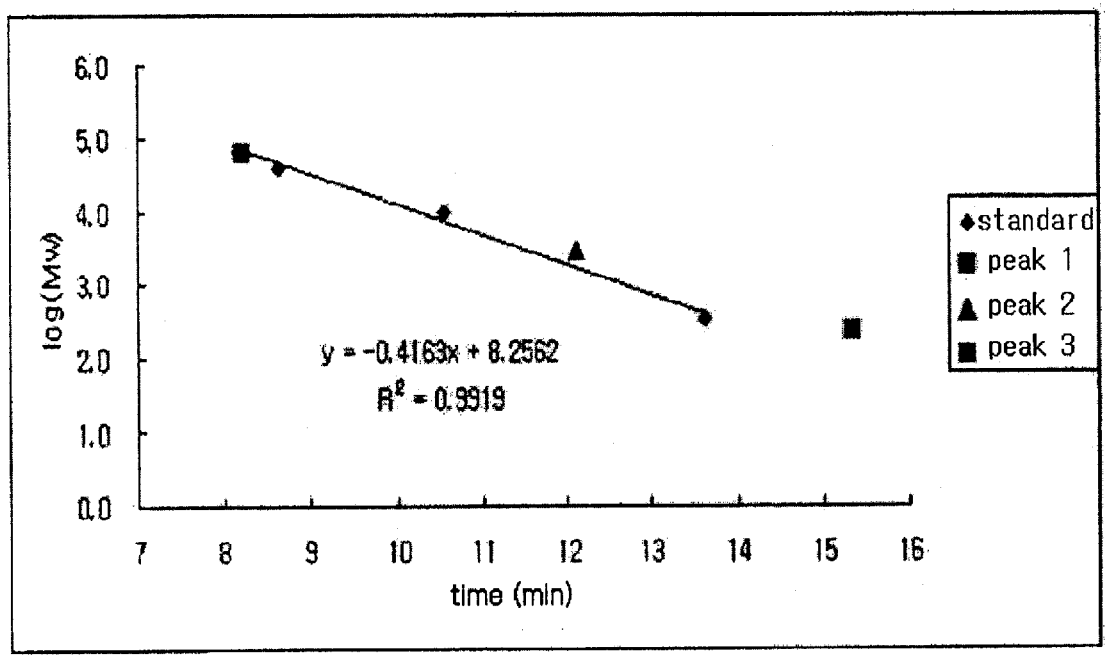

[Figure 15]
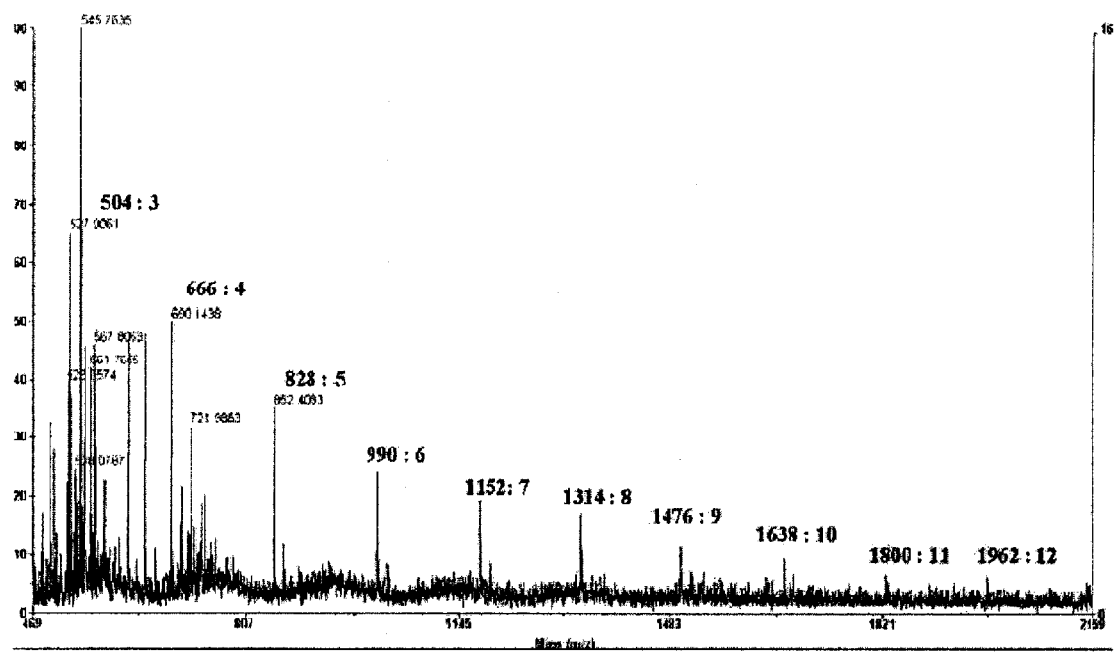
(A)
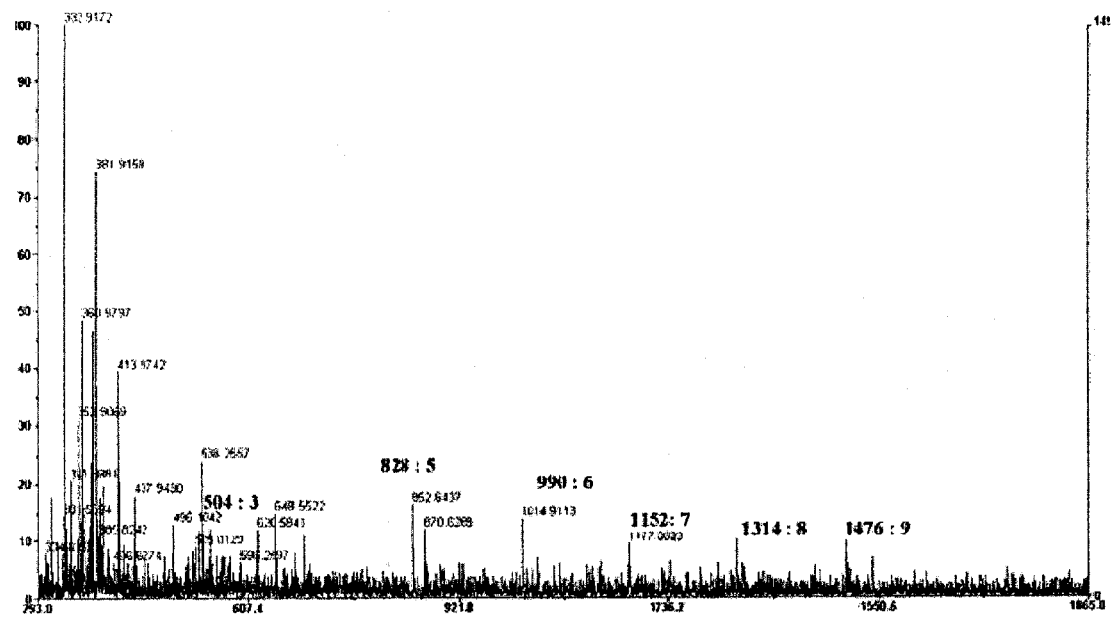
(B)

[Figure 16]
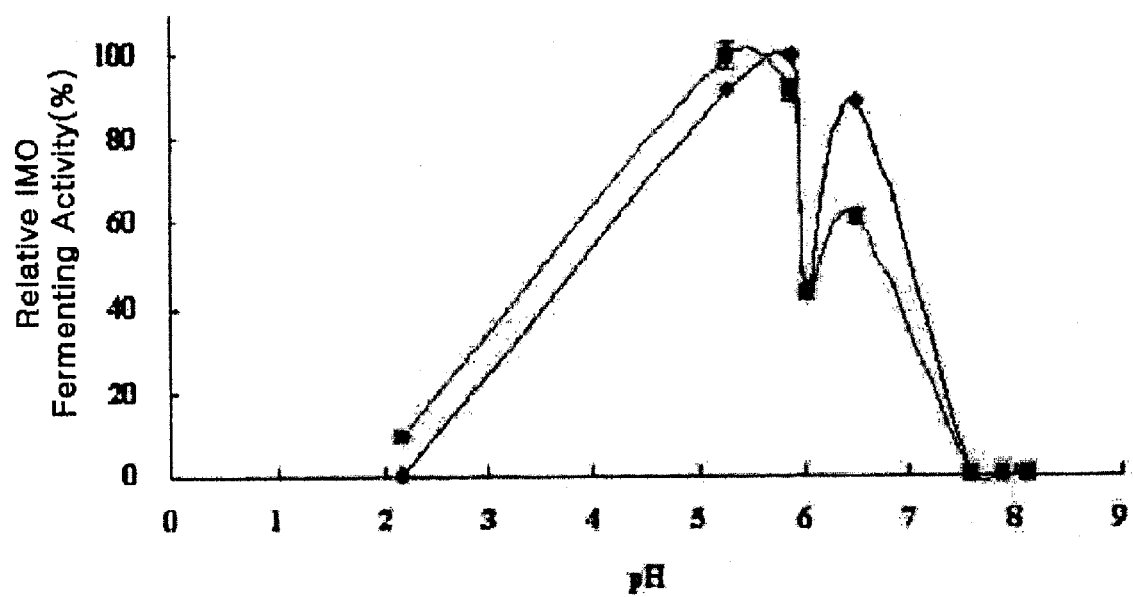

[Figure 17]
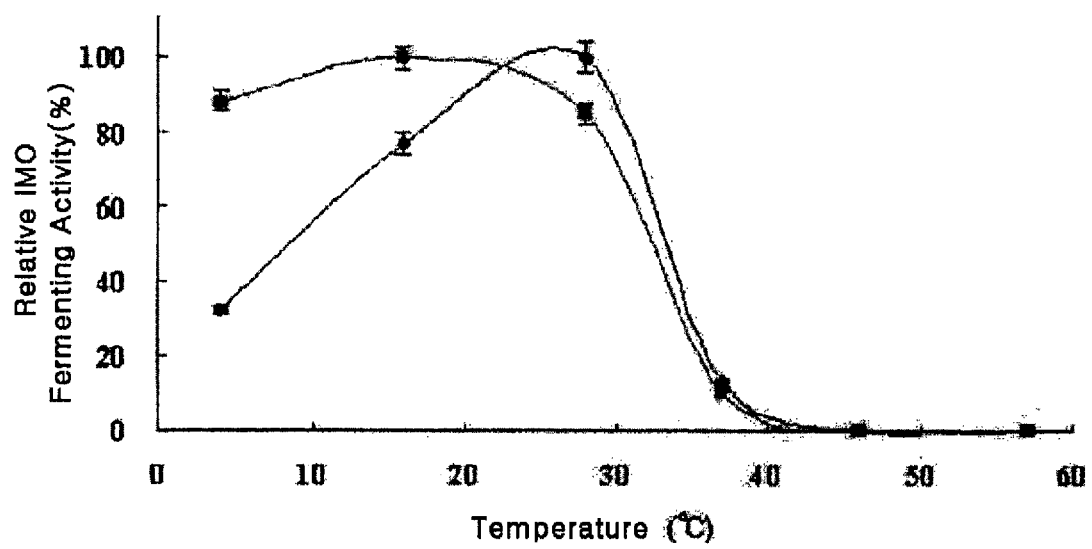

[Figure 18]
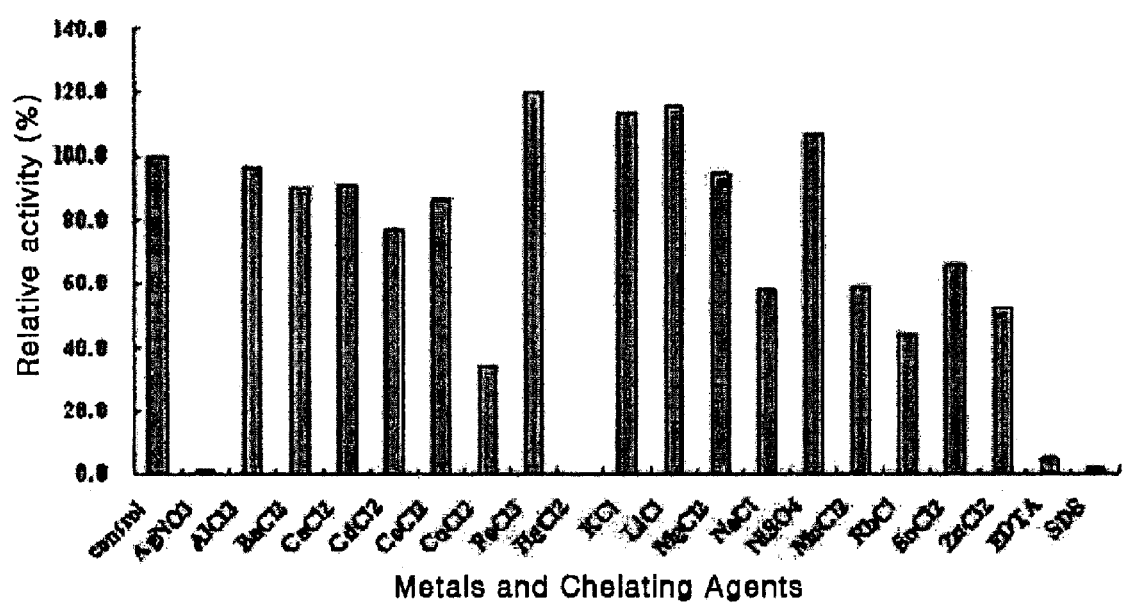

HYBRID GENES AND ENZYMES OF GLUCANASE AND DEXTRANSUCRASE AND PROCESSES FOR PREPARING ISOMALTO-OLIGOSACCHARIDES OR DEXTRAN USING THE SAME

PRIOR APPLICATIONS

This U.S. §371 National Phase patent application bases priority on International Application No. PCT/KR2007/002106, filed on Apr. 28, 2007, which in turn bases priority on Korean Application No. 10-2006-0038710, filed Apr. 28, 2006.

BACKGROUND OF THE INVENTION

1. Field of the Invention

The present invention relates to hybrid genes and enzymes of glucanase and dextransucrase, and to processes for preparing isomalto-oligosaccharides or dextran using the same. More specifically, the present invention relates to hybrid genes of glucanase and dextransucrase, recombinant vectors comprising said hybrid genes, microorganisms which are transformed with said recombinant vectors, hybrid enzymes which are expressed from said hybrid genes, and to process for preparing isomalto-oligosaccharides or dextran using said microorganisms or enzymes.

2. Description of the Prior Art

Recently, new kinds of sugar alternatives, "oligosaccharides," that are derived from natural food sources, have been developed by biotechnological methods, and used to prevent problems associated with over-consumption of sugar and sugar derivatives, including dental caries, obesity, diabetes, adult diseases and the like (see, Kim, K. S. and Y. H. Chae, 1997, The effects of addition of oligosaccharide on the quality characteristics of tomato jam, Korean J. Food Sci 27(2): 170-175). Unlike typical sugars that are degraded and absorbed in the form of monosaccharides by digestive enzymes present in human body, oligosaccharides taken as food materials are not readily degraded by digestive enzymes, thus producing less calorie compared to sucrose (see, Kim, K. S and Y. H. Chae, 1997, The effects of addition of oligosaccharide on the quality characteristics of tomato jam, Korean J. Food Sci 27(2): 170-175). Further, oligosaccharides have probiotic and seedling effects by promoting the growth of probiotic bacteria, *Bifidobacteria*, an inhibitory effect on the increase of blood glucose or cholesterol level (see, Zakia, S. and C. Andrieux, 1997, Compared effects of three oligosaccharides on metabolism of intestinal microflora in rat inoculated with a human fecal flora, Br. J. Nutr. 78: 313-324), and an inhibitory effect on synthesis of glucan that causes dental caries (see, Kim, K. S and Y. H. Chae, 1997, The effects of addition of oligosaccharide on the quality characteristics of tomato jam, Korean J. Food Sci 27(2): 170-175). Oligosaccharides include soybean-oligosaccharide, fructo-oligosaccharide, galacto-oligosaccharide, isomalto-oligosaccharide, etc. Isomalto-oligosaccharide is comprised at a small amount in soybean paste, soy sauce and rice wine, etc. It has a chemical structure wherein two or three saccharide residues are linked each other, and each saccharide residue is composed of one to six glucose molecules. Isomalto-oligosaccharide is known as a seasoning for foods and has the sweetness of about 50% compared to that of sucrose. Meanwhile, dextran is a polymer of D-glucose, having a molecular weight of about 4 million Daltons in its natural state. Dextran is used as a raw material for preparing syrup, etc., and further, it can be partially hydrolyzed by an acid and dissolved in a physiological saline at a concentration of about 6% for use as a serum substitute. Dextran, which has a molecular weight of from 5,000 to 100,000 Daltons, including one for use as a serum substitute, is called as 'clinical dextran.'

At present, various kinds of oligosaccharides are industrially produced either by the hydrolysis of polymers with an enzyme or an acid, or by the treatment of substrate with a glycosyl transferase. Moreover, for producing clinical dextran, a new method of mixed-culture fermentation has been developed. Compared to existing commercial methods for producing dextran that involve cultivation of microorganisms and acid-hydrolysis, the mixed-culture fermentation is simpler and gives a higher yield (see, Kim, D. and D. F. Day, 1994, A new process for the production of clinical dextran by mixed-culture fermentation of Lipomyces starkeyi and *Leuconostoc mesenteroides*, Enzyme Microb. Technol. 16: 844-848). The mixed-culture fermentation can be used to produce dextran with a desired low molecular weight by co-cultivating two kinds of bacteria, e.g., Lipomyces starkeyi which produces dextranase to hydrolyze dextran and *Leuconostoc mesenteroides* which produces dextransucrase to synthesize dextran, in a single fermentor. However, this method requires a delicate control for optimizing the growth of each bacterium and for suitably regulating the feed rate of sucrose.

Another method for producing oligosaccharides involves reacting sucrose substrate with dextransucrase and dextranase at the same time, thereby producing dextran by the action of dextransucrase and degrading the produced dextran by the action of endodextranase. When oligosaccharides are produced by using dextransucrase and dextranase, each strain producing each enzyme is cultivated separately, the resulting two enzymes are prepared separately, and then, the two enzymes are mixed in a ratio appropriate for obtaining a desired enzymatic activity or are prepared as immobilized enzymes for further use. However, this method requires a special mechanism for controlling the activities of said two enzymes.

Meanwhile, still another method involves immobilization of dextransucrase in various ways, reacting sucrose substrate with the immobilized dextransucrase, and then, degrading the thus obtained dextran with water-soluble dextranase. However, in the case of reacting the substrate with the two enzymes, some problems are occurred including that production yield of isomalto-oligosaccharides is significantly lower than the degradation rate of sucrose and production yield of polysaccharides are higher than that of isomalto-oligosaccharides. In addition, it requires a complicated technique for cultivating two strains separately and controlling activities of two enzymes simultaneously.

Under the circumstances, there has been a strong demand for a new method for simple and effective production of isomalto-oligosaccharides or low molecular weight dextran for clinical use from sucrose substrate by using a single bacterial strain or enzyme.

SUMMARY OF THE INVENTION

The present inventors have conducted extensive studies to develop a new process for producing isomalto-oligosaccharides or low molecular weight dextran for clinical use by using a single bacterial strain or enzyme. As a result, for the first time, the present inventors created hybrid genes of glucanase and dextransucrase, and found that hybrid enzymes obtained from said hybrid genes and microorganisms which produce said enzymes could be used to achieve said purpose of the invention, and therefore, completed the present invention. Thus, a purpose of the present invention is to provide hybrid genes of glucanase and dextransucrase, recombinant vectors comprising said hybrid genes, microorganisms which are transformed with said recombinant vectors, and hybrid enzymes which are expressed from said genes.

Another purpose of the present invention is to provide processes for preparing isomalto-oligosaccharides or dextran using said microorganisms or enzymes.

The first aspect of the present invention relates to hybrid genes in which genes for glucanase and dextransucrase are fused each other. The hybrid genes of the present invention may have the structure of either 5'-glucanse gene-linker DNA-dextransucrase gene-3' or 5'-dextransucrase gene-linker DNA-glucanase gene-3'. For the hybrid genes of the present invention, the glucanase gene can be gene dex2 from *Arthrobacter* sp., and the dextransucrase gene can be gene dsrB from Leuconostoc *mesenteroides* sp. A preferable hybrid gene of the present invention has the nucleotide sequence as set forth in SEQ ID NO: 1 or SEQ ID NO: 2.

The second aspect of the present invention relates to recombinant vectors comprising said hybrid genes.

The third aspect of the present invention relates to microorganisms which are transformed with said recombinant vectors.

The fourth aspect of the present invention relates to hybrid enzymes which are expressed from said hybrid genes.

The fifth aspect of the present invention relates to processes for producing isomalto-oligosaccharides or dextran, which comprise the step of cultivating said microorganisms in a sucrose-containing culture medium in the presence of an activator therefore.

The sixth aspect of the present invention relates to processes for producing isomalto-oligosaccharides or dextran, which comprise the step of reacting sucrose substrate with said hybrid enzymes.

BRIEF DESCRIPTION OF THE DRAWINGS

The invention can be best understood by those having ordinary skill in the art by reference to the following detailed description when considered in conjunction with the accompanying drawings in which:

FIGS. 3, 4, 5 and 6 represent a whole nucleotide sequence of the hybrid gene DXSR1 (dex2-dsrB) of the present invention;

FIGS. 7, 8, 9 and 10 represent a whole nucleotide sequence of the hybrid gene DXSR2 (dsrB-dex2) of the present invention;

FIG. 11 is a photograph of agarose gel electrophoresis for the PCR-amplified product of the hybrid gene of the present invention; FIG. 12 is a Thin Layer Chromatogram for the culture supernatant of *E. coli* that was transformed with the hybrid gene of the present invention;

FIG. 13 is a photograph of SDS-PAGE after staining for the cell lysates of *E. coli* that was transformed with the hybrid gene of the present invention;

FIG. 14 is a High Performance Liquid Chroraatogram for the culture supernatant of *E. coli* that was transformed with the hybrid gene of the present invention;

FIG. 15 shows the result of MALDI-TOF analysis for the reaction product between sucrose and the hybrid enzyme of the present invention;

FIG. 16 is a graph showing the relative activity and the production level of oligosaccharides of the hybrid enzyme of the present invention at different pHs;

FIG. 17 is a graph showing the relative activity and the production level of oligosaccharides of the hybrid enzyme of the present invention at different temperatures; and, FIG. 18 is a graph showing the relative activity and the production level of oligosaccharides of the hybrid enzyme of the present invention in the presence of various metal ions or chelating agents.

DETAILED DESCRIPTION OF THE PREFERRED EMBODIMENT

Hereinafter, the present invention will be described in more detail. According to the present invention, a gene for a new hybrid enzyme having activities of two different enzymes was created, the hybrid enzyme was expressed from said gene, and isomalto-oligosaccharides and low molecular weight dextran for clinical use were produced therefrom.

Specifically, according to the present invention, a gene coding for glucanase which has an activity of hydrolyzing dextran (glucan) and a gene coding for dextransucrase which has an activity of producing dextran from sucrose are obtained separately, and then, a recombinant expression vector comprising said two genes and a microorganism that is transformed with said recombinant vector are prepared using gene recombination methods. Genes coding for glucanase include gene dex2 from *Arthrobacter* oxydans KPS (KACC 91140), and for example, gene dex2 comprised in pAOD2 (KACC 95029) may be used. Genes coding for dextransucrase include gene dsrB from Leuconostoc *mesenteroides* NRRL B-1299, Leuconostoc *mesenteroides* NRRL B-1355, Leuconostoc *mesenteroides* NRRL B-512F, Leuconostoc *mesenteroides* NRRL B-742, or Leuconostoc *mesenteroides* NRRL B-1149, and especially, gene dsrB from Leuconostoc *mesenteroides* NRRL B-1299 may be used.

However, any genes, as long as they have the enzymatic activity of glucanase and dextransucrase, respectively, can be used regardless of their sources or nucleotide sequences, etc. Therefore, the above-described bacterial strains are just exemplary ones, and the scope of the present invention is not limited thereby. Specific processes for preparing the hybrid genes of the present invention are as described below.

Figure 1:
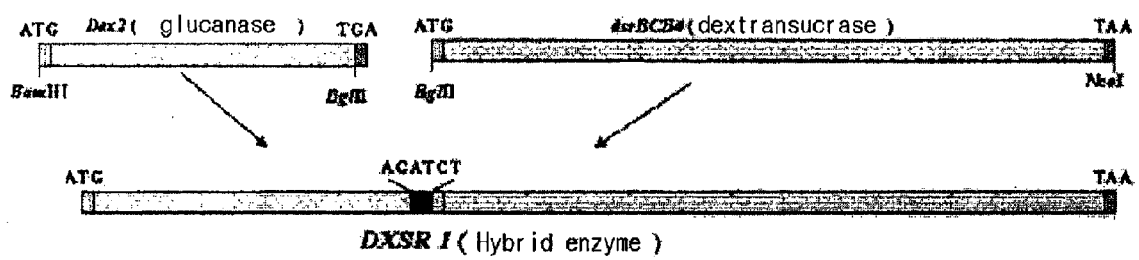
FIG. 1 is a schematic diagram for constructing the hybrid gene DXSR1 (dex2-dsrB) of the present invention.

First, total DNAs are isolated from an *Arthrobacter* sp. strain to obtain a glucanase gene from the *Arthrobacter* sp. strain. To isolate the glucanase gene, a gene amplification technique is used. Briefly, gene dex2 is amplified using a specially designed primer with excluding stop codon (TGA), and then, inserted to pRSETC expression vector for *E. coli*. Separately, the same procedure can be used for obtaining a dextransucrase gene from a Leuconostoc *mesenteroides* sp. strain. The obtained gene dsrB can be amplified using a specially designed primer, and then, inserted to a region between gene dex2 that have been already incorporated and pRSETC gene. A schematic diagram for constructing the hybrid genes in which gene dex2 and gene dsrB are fused in order is shown in FIG. 1, and their whole nucleotide sequences are shown in FIGS. 3, 4, 5 and 6 [SEQ. ID. NO: 1; blue bar: dex2 , red bar: a linker, black bar: dsrB, 6300 by including stop codon, 2099 aa, 234.3 kDa]. Alternatively, the obtained gene dsrB is amplified using a specially designed primer with substituting the 3' terminal sequence GTCGCT with AGATCT and excluding stop codon (TGA), and then, inserted to pRSETC expression vector for *E. coli*. The obtained gene dex2 is amplified using a specially designed primer excluding start codon (ATG), and then, inserted to a region between gene dsrB that have been already incorporated and pRSETC gene.

Figure 2:
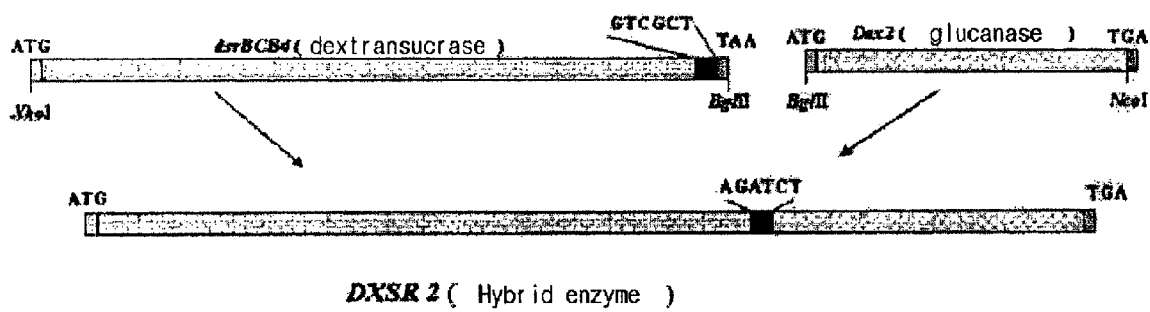
FIG. 2 is a schematic diagram for constructing the hybrid gene DXSR2 (dsrB-dex2) of the present invention.

A schematic diagram for constructing the hybrid genes in which gene dsrB and gene dex2 are fused in order is shown in FIG. 2, and their whole nucleotide sequences are shown in FIGS. 7, 8, 9 and 10 [SEQ. ID. NO: 2; blue bar: dex2, red bar: substituted sequence, black bar: dsrB, 6291 by including stop codon, 2096 aa, 234 kDa]. In the above-described processes, the linker DNA that is introduced at the flanking region of said two genes could be a sequence that is added to each of said two structural genes (for DXSR1), or a sequence with which a part of each structural gene is substituted (for DXSR2).

E. coli BL21, which is a bacterial strain for gene expression, is transformed with the obtained expression vector comprising said two genes. A maximum amount of the hybrid enzyme can be produced from the transformed strain when they are cultivated in a culture medium comprising yeast extract 5 g/(, trypton 10 g/(, NaCl 5 g/<and sucrose 20 q/1. Further, the hybrid enzyme has a maximum activity when lactose (ImM) is added to the medium at OD600 of 0.5 as an activator.

According to the present invention, by cultivating microorganisms carrying said hybrid genes in a sucrose-containing medium in the presence of an activator, the hybrid enzymes are obtained, and at the same time, isomalto-oligosaccharides or low molecular weight dextran for clinical use are obtained from the sucrose contained in said medium. Meanwhile, by directly reacting sucrose with said hybrid enzymes, isomalto-oligosaccharides or low molecular weight dextran for clinical use can be produced. The hybrid enzyme employs sucrose as its substrate, transfers the glucosyl residue of sucrose to yield dextran by its dextransucrase activity. The resulting dextran is degraded by the activity of glucanase to yield isomalto-oligosaccharides or low molecular weight dextran for clinical use.

The isomalto-oligosaccharides or low molecular weight dextran for clinical use that are prepared according to the present invention can be useful in the industrial fields of food, cosmetics, pharmaceuticals, etc.

In addition, based on the glucosyl transferase activity of the hybrid enzymes, they can be used for preparing many novel materials for clinical use having new structures and characteristics from different kinds of receptors.

Hereinafter, the present invention is described in more detail based on the following examples. However, these examples should not be construed to limit the scope of the present invention in any manner.

EXAMPLE 1

Preparation of the Hybrid Gene of Glucanase-Dextransucrase (1) Isolation of Chromosomal DNA Comprising the Genes of Glucanase and Dextransucrase Gene dex2 and gene dsrB were isolated from *Arthrobacter oxydans* KPS (KACC 91140) and *Leuconostoc mesenteroides* NRRL B-1299 (USDA), respectively, by alkaline lysis method.

Specifically, *Leuconostoc mesenteroides* NRRL B-1299 was cultivated in 50 ml of LWS medium [0.5% (w/v) yeast extract, 0.5% (w/v) KH2PO4, 0.02% (w/v) MgSO4-7H2O, 0.001% (w/v) NaCl, 0.001% (w/v) FeSO4-7H2O, 0.001% (w/v) MnSO4-H2O, 0.013% (w/v) CaCl2-2H20], and *Arthrobacter oxydans* KPS was cultivated in 50 ml of LB medium [0.5% (w/v) yeast extract, 0.5% (w/v) NaCl, 1% trypton], for two days. The cells were harvested by centrifugation at 14000 xg at a temperature of 10° C. for 10 minutes. The cultures of two strains were added to an E-tube, respectively. Cells were then washed with 50 mM Tris-Cl (pH 8.0, 10 mi) and centrifuged at 14000 xg for 2 minutes. The same procedure of washing and centrifugation was repeated one more time. Lysozyme solution of 5 mi was added to the cells, and the mixture was stored at 37° C. for one hour. Thereto were added 25% sucrose (3 mi), TES buffer (175 µi), 20% SDS and 0.5 mM EDTA (100 µi), and the mixture was allowed to stand at 37° C. for 30 minutes. 40 µi of RNase V (10 mg/mi in TE buffer) was added thereto, and the mixture was allowed to stand at 37° C. for 20 minutes. For deproteinization, 250 µi of Proteinase K (10 mg/m# in TE buffer) was added thereto and the mixture was stored at 50° C. for one hour. 900 µi of 5 M NaCl was added thereto and the mixture was centrifuged at 14000 xg for 10 minutes. To the supernatant collected from the centrifuge, a phenol extracting solution of the same volume as the supernatant was added thereto and the resulting mixture was centrifuged at 14000 xg for 1 minute for three times. Anhydrous alcohol was added thereto at a two-fold amount of the supernatant, and the reaction was performed for 12 hours. The reaction mixture was centrifuged at 14000 xg at a temperature of 4° C. for 15 minutes and washed with 1 m£ of 70% alcohol, and the resulting mixture was centrifuged at 14000 xg at a temperature of 4° C. for 3 minutes. The supernatant was discarded therefrom and the residue was dried under vacuum for 10 minutes. The dried residue was then dissolved in triple-distilled water. The isolation of the chromosomal DNA for the two strains was confirmed by U/V agarose gel electrophoresis (0.7%) for the 3 µi sample.

(2-i) Amplification of Glucanase and Dextransucrase Genes (i)

Each gene of glucanase and dextransucrase was amplified by using the chromosomal DNA obtained in the above (1) as a template and a primer designed for amplification of said two genes. Specifically, for amplifying the gene of glucanase, two primers of 5'-5 attttatctcgagttatgctgtctatga-3' (SEQ ID NO: 3) and 5'-ggcttttttagttaagatcttgagaca-3' (SEQ ID NO: 4) were used. For amplifying the gene of dextransucrase, two primers of 5' gatcgatggatcagatctaagcattac-3' ( SEQ ID NO: 5) and 51-atcaagcttcgaattccatggtaccc-3' (SEQ ID NO: 6) were used. Conditions for the amplification were as follows.

Reaction was performed in the presence of the gene (2 µi), each primer (2 µl), dNTP (0.2 mM), MgCl2 (2 mM), 10× buffer (Mg2+-free, 5 µJt), Taq polymerase (0.05 U/µJL) and triple-distilled water (30.5 µi). Time and temperature for denaturation were 40 seconds and 94° C. for glucanase gene and 60 seconds and 94° C. for dextransucrase gene, respectively. The primer was annealed at 52° C. for 40 seconds for glucanase gene and at 53° C. for 1 minute for dextransucrase gene. Time and temperature for the amplification were 2 minutes and 72° C. for glucanase gene and 4 minutes 40 seconds and 72° C. for dextransucrase gene, respectively. The desired PCR-amplified product was identified by agarose gel electrophoresis with 1 kb DNA ladder (Promega, USA) for the 3 µJL sample.

(2-ii) Amplification of Glucanase and Dextransucrase Genes (ii)

The procedure as described in the above step (2-i) was repeated except that primers of 5'-attttatctcgagttatgctgtc-tatga-3 (SEQ ID NO: 7) and 5'-ggcttttttagttaagatcttgagaca-3' (SEQ ID NO: 8) were used for amplifying the gene of dextransucrase, and primers of 5'-gatcgatggatcagatctaagcattac-3' (SEQ ID NO: 9) and 5'-atcaagcttcgaattccatggta-3' ( SEQ ID NO: 10) were used for amplifying the gene of glucanase.

(3) Preparation of the Hybrid Genes of Glucanase and Dextransucrase

The PCR-amplified product obtained from the above step (2) was subjected to agarose gel electrophoresis with 1 kb DNA ladder (Promega, USA). The DNA bands of 1.8 kb (glucanase gene) and 4.4 kb (dextransucrase gene) were cleaved from the gel and transferred to an Eppendorf tube, respectively. The DNA was purified using AccuPrep Gel purification Kit [Bioneer, KOREA] and then digested with restriction enzymes {BamH1 and BgI π it or BgI II and Nco I for glucanase gene; BgI H and Nco I or Xho I and BgI II for dextransucrase gene}. The resulting mixture was subjected to agarose gel electrophoresis, the DNA bands were cleaved, and the cleaved DNA bands were transferred to an Eppendorf tube, respectively. The DNA was purified using AccuPrep Gel purification Kit [Bioneer, KOREA] and then digested with the restriction enzymes. The resulting DNA was ligated to pRSETC vector (Invitrogen, USA), which has been digested with the same restriction enzymes as those used for said genes. Specifically, the ligation was carried out in a total volume of 10 μi (7 μi of DNA to be inserted, 1 μi of vector DNA, 1 μi of 1 Oxligation buffer, 1 μi of T4 DNA ligase) at 16° C. for 16 hours to prepare a recombinant vector comprising the hybrid gene of glucanase and dextransucrase. The ligated DNA (10 μi) was added to *E. coli* BL21 (Novagen, USA) cells which are competent cells for transformation. The resulting mixture was kept on ice for one hour. In order to disrupt cell walls and to incorporate the desired DNA to the cells, the cells were subjected to heat shock treatment at 42° C. for 90 seconds. LB medium (1 mi) was then added thereto and the cells were incubated for one hour at 37° C. Subsequently, the obtained culture was cultivated in LB medium supplemented with 2% sucrose and ampicillin (50 μg/'μi) at 37 "C for 8 hours. Then, the culture was incubated at 28° C. for 16 hours to collect non-viscous colonies. According to the procedure described in the above step (1), the recombinant gene was obtained from the resulting cells and then amplified by gene amplification method.

FIG. 1 schematically represents the construction of the hybrid gene DXSR1 (6300 bp) which consists of glucanase gene of 1860 bp, linker DNA of 6 bp and dextransucrase gene of 4434 bp. FIGS. 3, 4, 5 and 6 represent a whole nucleotide sequence of the hybrid gene DXSR1 of the present invention.

In addition, FIG. 2 schematically represents the construction of the hybrid gene DXSR2 (6291 bp) which consists of dextransucrase gene of 4431 by (six nucleotides at 3' terminus were substituted with the linker DNA) and glucanase gene of 1860 bp.

FIGS. 7, 8, 9 and 10 represents a whole nucleotide sequence of the hybrid gene DXSR2 of the present invention.

FIG. 11 is a photograph of agarose gel electrophoresis for the PCR-amplified product of the hybrid gene DXSR1, which shows the presence of the hybrid gene of about 6.3 kb [Lane 1, DNA size marker (10000 bp, 8000 bp, 6000 bp, 5000 bp, 4000 bp, 3000 bp, 2500 bp, 2000 bp, 1500 bp, 1000 bp, 750 bp, 500 bp); Lane 2, PCR product of the hybrid gene].

EXAMPLE 2

Cultivation of the Cells Transformed with the Hybrid Genes

The transformed cells comprising the hybrid gene DXSR1, which was obtained from the above step 1(3) were cultivated in LB medium [0.5% (w/v) yeast extract, 0.5% (w/v) NaCl, 1% trypton] supplemented with 2% sucrose and ampicillin (50 βg/βi) at 37° C. for six hours. Then, lactose (1 mM) was added thereto as an activator and the cells were cultivated at 16 "C for 24 hours. Supernatant obtained from said cell culture and cell lysates obtained by ultra-sonication of said cell culture were used for identification of the enzymatic activity.

EXAMPLE 3

Identification of the Hybrid Enzymes and the Reaction Product

The components of the supernatant of the cell culture obtained from Example 2 were identified by TLC. The result is shown in FIG. 12. In FIG. 12, lane 1 represents a result for a series of isomalto-oligosaccharides, lane 2 represents a result for sucrose, and lane 3 represents a result for the culture supernatant. As shown in FIG. 12, it was found that isomalto-oligosaccharides, which were degraded from sucrose, were contained in the culture supernatant.

Furthermore, in order to determine the presence of the hybrid enzymes in the obtained cell lysates, 6% SDS-PAGE electrophoresis was carried out. Specifically, the lysates were subjected to an electrophoresis with electric current of 50 mA on 6% polyacrylamide gel. Upon the completion of the electrophoresis, the gel was stained with a staining solution (Coomassie brilliant blue R-250 of 1 g, acetic acid of 100 mi, methanol of 450 mi and distilled water of 450 mi), and then, de-stained with a de-staining solution (methanol of 100 mi, acetic acid of 10 mi and distilled water of 800 mi). The de-staining was performed three times with the de-staining solution of about 300 mi per time. Molecular weight of each resolved protein was determined in reference with standard proteins purchased from Bio-Rad (USA; kDa—myosin 200, β-galactosidase 116, phosphorylase b 97.4, serum albumin 66.2, ovalbumin 45, carbonic anhydrase 31, trypsin inhibitor 21.5, lysozyme 14.4, aprotinin 6.5 kDa).

In order to identify an active band on the gel, the gel subjected to SDS-PAGE (under non-denaturing condition) was washed with 20 mM sodium acetate buffer (pH 5.2) for one hour. The washed gel was immersed in a sucrose solution (100 mM) to carry out the enzymatic reaction at 28° C. for 16 hours. Then, according to Periodic acid-Schiff (PAS) method, the active band was identified. The result is shown in FIG. 13. In FIG. 13, lane M represents a standard protein marker; lane 1 represents a staining result for the enzymes comprising the hybrid enzyme,—lane 2 represents a result of electrophoresis of the hybrid enzyme on a gel comprising 1% blue dextran to show the band having glucanase activity; lane 3 shows the electrophoretic band of the hybrid enzyme having the activity of synthesizing polysaccharides and oligosaccharides upon reaction with sucrose.

Meanwhile, HPLC analysis was carried out to identify the components of the culture supernatant. The result is shown in FIG. 14.

EXAMPLE 4

Identification and Characterization of Enzymatic Activity of the Hybrid Enzyme

The reaction product between the hybrid enzyme obtained from Example 3 and sucrose as a substrate was analyzed according to MALDI-TOF method. The result is shown in FIG. 15 [(A) MALDI-TOF analysis result for a series of isomalto-oligosaccharides; (B) MALDI-TOF analysis result for the reaction product between the hybrid enzyme of the present invention and sucrose]. It was confirmed from FIG. 15 that the hybrid enzyme of the present invention hydrolyzed sucrose to isomalto-oligosaccharides. Meanwhile, the relative enzymatic activity and the production level of oligosaccharides from the reaction with the substrate (sucrose) of the hybrid enzyme of the present invention were determined at various pHs. The result is shown in FIG. 16. FIG. 16 shows the residual activity of the hybrid enzyme (■) upon storage at various pHs and the production level of oligosaccharides (♦) from the reaction with the substrate at various pHs.

As shown in FIG. 16, the hybrid enzyme of the present invention has a rather low activity around pH 6, while it has a maximum activity at a pH ranging from 5 to 6.5. This could be because glucanase is stable at a neutral pH while dextransucrase is stable at a low pH, and so both enzymes have a relatively low activity at pH 6.0, in the middle of these pHs.

Furthermore, the relative enzymatic activity and the production level of oligosaccharides from the reaction with the substrate (sucrose) of the hybrid enzyme of the present invention were determined at various temperatures. The result is shown in FIG. 17. FIG. 17 shows the residual activity of the hybrid enzyme (■) upon storage at various temperatures and the production level of oligosaccharides (♦) from the reaction with the substrate at various temperatures. As shown in FIG. 17, it was found that the hybrid enzyme of the present invention has the maximum activity at a temperature ranging from about 15 to about 30° C.

Still furthermore, the production level of oligosaccharides from the reaction with the substrate (sucrose) was measured in the presence of various metal ions or chelating agent. The result is shown in FIG. 18. As shown in FIG. 18, it was found that metal ions such as $Fe^{3+}$, $K+$ and $Li+$ increase the oligosaccharides-producing activity, while $Ag+$, $Hg^{2+}$, EDTA, SDS, etc. nearly abolish the oligosaccharides-producing activity.

According to the present invention, expensive isomalto-oligosaccharides and low molecular weight dextran for clinical use can be produced simply and effectively from cheap substrate, sucrose, using a single strain or enzyme.

BRIEF DESCRIPTION OF THE SEQUENCES

SEQ ID NO 1: represents a nucleotide sequence of the hybrid gene of dex2 derived from the organism *Arthrobacter oxydans* 16S, and dsrB derived from the organism *Leuconostoc mesenteroides* NRRL B-1299, in order.

SEQ ID NO 2: represents a nucleotide sequence of the hybrid gene of dexB derived from the organism *Leuconostoc mesenteroides* NRRL B-1299, and dsr2 derived from the organism *Arthrobacter oxydans* 16S, in order.

SEQ ID NO: 3 represents a nucleotide sequence of the primer dex2FBamH I for the amplification of glucanase gene.

SEQ ID NO: 4 represents a nucleotide sequence of the primer dex2RBgl II for the amplification of glucanase gene.

SEQ ID NO: 5 represents a nucleotide sequence of the primer dsrBFBgl II for the amplification of dextransucrase gene.

SEQ ID NO: 6 re resents a nucleotide sequence of the .rimer dsrBRNco I for the amplification of dextransucrase gene.

SEQ ID NO: 7 represents a nucleotide sequence of the primer dsrBFXho I for the amplification of dextransucrase gene.

SEQ ID NO: 8 represents a nucleotide sequence of the primer dsrBRBgl II for the amplification of dextransucrase gene .

SEQ ID NO: 9 represents a nucleotide sequence of the primer dex2FBgl II for the amplification of glucanase gene.

SEQ ID NO: 10 represents a nucleotide sequence of the.rimer dex2RNco I for the amplification of glucanase gene.

What is claimed is:

1. A hybrid gene comprising a gene encoding glucanase and a gene encoding dextransucrase fused together; wherein the glucanase gene is a gene from *Arthrobacter* sp., wherein the dextransucrase gene is a gene from *Leuconostoc* sp., and wherein the expression product of said hybrid is a hybrid enzyme capable of producing isomalto-oligosaccharides or dextran.

2. The hybrid gene of claim 1, comprising a structure of either 5'-glucanase gene-linker DNA-dextransucrase gene-3' or 5'-dextransucrase gene-linker DNA-glucanase gene-3'.

3. The hybrid gene of claim 1, wherein the glucanase gene is gene dex2 from *Arthrobacter* sp.

4. The hybrid gene of claim 1, wherein the dextransucrase gene is gene dsrB from *Leuconostoc mesenteroides* sp.

5. The hybrid gene of claim 3, wherein the nucleotide sequence of the glucanase gene is SEQ ID NO: 1.

6. The hybrid gene of claim 4, wherein the nucleotide sequence of the dextransucrase gene is SEQ ID NO: 2.

7. A recombinant vector, comprising the hybrid gene of claim 1.

8. A process for producing isomalto-oligosaccharides or dextran, the process comprising:
    cultivating a microorganism comprising a hybrid gene according to claim 1 in a sucrose-containing culture medium in the presence of an activator; and
    reacting a sucrose substrate with a hybrid enzyme expressed from the hybrid gene of claim 1.

9. An isolated microorganism transformed with the recombinant vector of claim 7.

10. An isolated microorganism comprising the hybrid gene of claim 1.

11. A process for producing a hybrid enzyme encoded by the hybrid gene of claim 1, comprising:
    providing a microorganism comprising the hybrid gene of claim 1; and
    cultivating the microorganism under conditions whereby a hybrid enzyme is expressed from said hybrid gene.

12. An isolated microorganism comprising the hybrid gene of claim 2.

13. An isolated microorganism comprising the hybrid gene of claim 3.

14. An isolated microorganism comprising the hybrid gene of claim 4.

15. An isolated microorganism comprising the hybrid gene of claim 5.

16. An isolated microorganism comprising the hybrid gene of claim 6.

17. A process for producing a hybrid enzyme encoded by the hybrid gene of claim 2, comprising:
    providing a microorganism comprising the hybrid gene of claim 2; and
    cultivating the microorganism under conditions whereby a hybrid enzyme is expressed from said hybrid gene.

18. A process for producing a hybrid enzyme encoded by the hybrid gene of claim 3, comprising:
    providing a microorganism comprising the hybrid gene of claim 3; and
    cultivating the microorganism under conditions whereby a hybrid enzyme is expressed from said hybrid gene.

19. A process for producing a hybrid enzyme encoded by the hybrid gene of claim 4, comprising:
    providing a microorganism comprising the hybrid gene of claim 4; and
    cultivating the microorganism under conditions whereby a hybrid enzyme is expressed from said hybrid gene.

20. A process for producing a hybrid enzyme encoded by the hybrid gene of claim 5, comprising:
    providing a microorganism comprising the hybrid gene of claim 5; and
    cultivating the microorganism under conditions whereby a hybrid enzyme is expressed from said hybrid gene.

21. A process for producing a hybrid enzyme encoded by the hybrid gene of claim 6, comprising:
    providing a microorganism comprising the hybrid gene of claim 6; and
    cultivating the microorganism under conditions whereby a hybrid enzyme is expressed from said hybrid gene.

* * * * *

SEQUENCE LISTING

```
<160> NUMBER OF SEQ ID NOS: 10

<210> SEQ ID NO 1
<211> LENGTH: 6300
<212> TYPE: DNA
<213> ORGANISM: Artificial Sequence
<220> FEATURE:
<223> OTHER INFORMATION: Hybrid gene of dex2 and dsrB

<400> SEQUENCE: 1
atgaagcatt  acctccgtct  attggcctca  gcatttgcgc  tgctgctcct  gctgccggct      60
gccggccagg  agccagccgc  tgcgacagaa  cagaccggtt  tcactgccac  cggacccggc     120
cttcggacct  ggtggcacaa  caactacgaa  tacaacccaa  cctcacccac  ccagaacggc     180
acagtccgcc  ggtcatcctt  ttacgaggtg  caagtagcca  cagcaacggc  accaggaacg     240
cgctacgact  ccttcgccta  catgagcatt  ccccgcagcg  gaaaggggaa  gaccggctac     300
acggagccgg  acggagcaga  gttctcttcg  tcagcgaacc  tctcaatgag  ctggtccagc     360
tttgagtact  caacggacgt  ctgggtggac  gtcaaactca  cgacaggcca  aacaatcacg     420
tctgtggatc  aggtaacgat  ccggcccagc  aagtacacct  tcgagaaaga  gctggtgaac     480
cccagcacca  tccgggtcaa  agtcccctac  tcgtcgacgg  gctaccggct  ctcagtggaa     540
ttcgcgcccc  agctcttcac  tgcatacaac  gacatgtccg  gaacggcggg  ggtgttgact     600
gaaaccggtg  gcggggatca  ccgcgccatc  cataccgaac  cacggaattc  catgatgatc     660
ttcgccgagc  cgaccctggg  cggcggcgag  gcggagcggt  tgattcccac  ctccgcatcc     720
ggagctatca  actatccgca  ggaaggcctg  gtcgacaacc  tggggtcggt  caccgaggag     780
```

| | |
|---|---|
| atcatctact tccggcccgg gacgtattac atgggatcgg accaccgggc ctcgatgccg | 840 |
| cccaacgtca aatggatcta cctggctccc ggggcgtatg tcaaaggtgc cttctacttc | 900 |
| cccaactcga cgcagggcgt ctacaaggtc actggccgcg gcgtgctctc cggcgaacag | 960 |
| tacgtctatg aagccgatac aaccaccagc gggtacacgc attcaaccgg cgctaattgc | 1020 |
| cacaacacct gcgtgaagat gctggaattc acgtcttcat cgaccatgca gcagtacttg | 1080 |
| gacgtggagg gaatcaccat cagcgaacct ccctaccact cctttgtcat ttacgggccg | 1140 |
| caaaacgcct atgagatgga atgcgggtg gataactaca agcaggtggg cagctggtac | 1200 |
| tggcagaccg acgggatgga actctacgag ggcgggcgga tgaacaacac ctttttccac | 1260 |
| tccaatgatg acgtcctgaa gctctaccac agcaacgtga cggtggataa cacggtgatc | 1320 |
| tggaagaacg agaacggtcc ggtcatccag tggggttggg cgccgtacaa cattgacaat | 1380 |
| gtggtcgtca ccaacacaga cgtcatccac aaccgcatgt attggaagga cgtcaaatac | 1440 |
| aacacctgca tcatcaactc gtcctcccac tacgcggaca tgggctcctc cacccacggcg | 1500 |
| aaccccgcca ccacgatcag gaatttccgg ctggagaaca ttactgtcga aggaatgacc | 1560 |
| aactgcgccc tcaggatcta tgcgcttttcc aacaccgaga acatccacat caagaacctg | 1620 |
| aatatcggaa gctggaacgg gttggaccac acgtcccagg tgagccacct gaagcgctat | 1680 |
| tcagacactg ccaacaacaa ggtctggctg ggcaacgaga ctgtcgacag cagaggcatc | 1740 |
| aagctcgaga actacaccgt cggcggggcc aggatcgaca aaaccacgac caactggagc | 1800 |
| gataaccagg cgggccgtct cggcttcgac ggcgaaaact gggataactg gaacgcgtgg | 1860 |
| agatctatgc tgtctatgac cgctacttca caaaatgtta atgcagatag cacaaacaca | 1920 |
| gtgacggata agtcagttac tgtctccaat aattcgaata caaccaatca acacgatact | 1980 |
| gtcgttgaca aacaaacgat acctgtcaaa aatgaccaaa caacacaaca atcgccgca | 2040 |
| aatgccaccc aagcagaaaa agtaaaagca tcagacacaa cgactgatac gcaaaagcaa | 2100 |
| gctgaaacgg caaacaacac taacaaggat tcgatagata atctcaccaa gcagttgccg | 2160 |
| gctgttacac caacagctaa tcaaaaaact ggttatctgg aaaaagatgg taaatggtac | 2220 |
| tatgtaacca gtgataacac acttgctaag gggttgacta ctgttgacaa ccacaagcag | 2280 |
| tattttgaca caatggcgt gcaggcaaaa ggccaattcg ttaccgataa cagtaaaaca | 2340 |
| tactatctcg atcctaactc cggtaacgca gtaaccggga tacaacaaat tggctcacaa | 2400 |
| acattagcct tcaatgacaa cggtgaacaa gttttgctg atttctatac agcgccagat | 2460 |
| ggcaaaactt attattttga cgataaagga caagcaacta ttggtctaaa ggccattaat | 2520 |
| gggcacaatt attacttcga tagtttggga caactaaaaa aaggatttac cggtgtcatt | 2580 |
| gacggtcaag tacgctattt tgatcaagaa tcaggacaag aggtatcaac aaccgactca | 2640 |
| caaatcaaag aaggtttaac ttctcagaca acagactata cagcacataa tgccgttcac | 2700 |
| agcaccgata gcgctgattt cgacaatttt aatggttatt tgaccgcttc ttcatggtat | 2760 |
| cgccctaaag atgttttaag aaatggtcaa cactgggaag caacaacagc taatgacttc | 2820 |
| cggcccattg tgtcagtttg gtggcctagc aagcaaacac aagtaaatta cctaaactac | 2880 |
| atgtctcaaa tgggactcat tgacaatcgt cagatgttct cgctaaaaga caatcaagcc | 2940 |
| atgttgaata ttgcttgcac aacagtccaa caagcaattg aaacaaaaat cggtgtggct | 3000 |
| aatagtacag catggcttaa aacagccatt gatgatttca ttcgtacaca gccacaatgg | 3060 |
| aacatgtcga gtgaagatcc caaaaatgat catttacaaa acggcgcttt gactttcgtc | 3120 |
| aacagtccat tgacaccaga tactaactct aatttcagac tattaaatcg cacaccaaca | 3180 |

```
aaccagacag gtgtgccaaa atatacaatt gatcaatcta agggtggttt tgaactctta    3240
ctcgctaatg atgtagacaa ctctaatcct gttgtgcaag ctgagcagtt aaattggtta    3300
cactatttga tgaattttgg tagcattaca gcaaacgatt ctgctgctaa ttttgatggg    3360
atacgtgtcg atgctgtcga taatgttgac gctgatttac tccagattgc agcagattat    3420
ttcaaagctg cttatggtgt tgataaaaat gacgcaacag caaatcaaca tctttcaatt    3480
cttgaagatt ggagccataa cgaccctgaa tacgtgaagg attttggtaa taatcaactc    3540
acaatggatg attacatgca tacccagtta atctggtcct tgactaaaga tatgcgtatg    3600
cgtggtacca tgcaacgctt catggactat tacctcgtca atcgcaatca cgatagtacc    3660
gaaaacactg ccattccaaa ttacagcttt gttcgcgcac acgatagtga agtacaaaca    3720
gtcattgctc aaattatttc tgagttacat cccgacgtaa aaaatagttt ggcaccaaca    3780
gcagaccagc tagccgaagc ctttaaaatt tataataacg atgaaaaaca ggcggataag    3840
aaatatacac aatacaacat gcctagcgcc tatgcgatgc tgttaactaa taagatacaa    3900
gtaccgcgcg tttattatgg tgatttatac accgatgatg tcaatatat ggcaaataag     3960 tccccttatt ttgatgccat caacggcttg ctaaagtcac gtatcaaata tgttgctggt    4020
ggtcagtcaa tggctgttga tcaaaacgat atcctgacaa atgttcgtta tggtaaaggt    4080
gccatgagtg tgacagatag cggtaatgca gacacacgaa cacaaggtat tggtgtgatt    4140
gtcagtaata agaaaatct ggccttaaaa tcaggcgaca cggtgacatt acacatgggt     4200
gccgctcaca aaaatcaagc attcagatta ttattaggga caactgctga caatttgtct    4260
tattatgata tgacaacgc cccagtaaag tacaccaatg atcagggcga tttaatttt     4320 gataatactg aaatctatgg tgtccgtaac ccgcaagtct ctggcttctt agctgtttgg    4380
gtgcctgttg gggctgacag ccatcaagac gcgcgtactt tgtctgacga cacagcccat    4440
catgatggca aaaccttcca ctcaaatgct gctttagatt ctcaggttat ttacgaaggt    4500 tttttcaaatt tccaagcttt tgccacaaac actgaagact atacaaatgc tgtcattgca    4560
aaaaatggtc agttattcaa agattggggt atcacaagtt tccagttggc accacaatat    4620
cgttcaagca ccgataccag tttcttagat tcaattatcc aaaatggtta tgcctttaca    4680
gatcgttatg atttaggcta cggtacacca acaaaatatg gcacagttga ccagttacgc    4740
gatgccatca aggctctgca cgcaaatggc atccaagcaa tcgctgactg ggtacccgac    4800
caaatttata atttaccggg tcaagaatta gcgaccgtca cccgaacaaa ctcttatggt    4860
gataaagaca ctaactcaga tattgatcag tcactatatg tcatacaaag tcgtggtggt    4920
ggtaaatacc aagcacagta tggcggtgcc ttcttatccg atatccagaa aaaatatcca    4980
gcacttttcg aaacaaaaca aatttctaca gggctaccta tggatcctag tcagaaaata    5040
acagaatggt ctggtaaata ctttaatggc tcaaatattc aaggcaaagg ggctggctat    5100
gtcttgaaag acagtggtac cgatcaatac tataaggtta catcaaacaa taataatcgt    5160
gacttcttgc aaaacaatt aacgatgac ttatctgaaa ccggatttgt ccgcgataac     5220
attggtatgg tctattacac actgagtggc tatctagctc gaaacacctt tatacaagat    5280
gataatggca attattatta ctttgatagc accggccatc tcgttactgg cttccagaat    5340
attaataacc atcactattt cttcctacca acggtattga aactcgttca atctttctta    5400
cagaatgctg acggttcaac gatttatttt gaccaaaaag ggcgtcaagt atttaatcaa    5460
tacattactg accaaaccgg taccgcctat tacttccaga atgatggcac aatggtcact    5520
tctggcttca ctgaaatcga tggtcataag caatacttct acaagaacgg cacacaagtc    5580
```

-continued

| | |
|---|---|
| aaagggcaat tgtatcaga cactgatggt cacgttttct acttagaagc tggtaacggc | 5640 |
| aacgtggcga cacaaagatt tgcacaaaat agtcaaggtc agtggttcta tttgggtaat | 5700 |
| gatggcattg ccttgactgg tttgcaaaca atcaatggtg ttcaaaatta tttctacgcc | 5760 |
| gatggtcatc aaagtaaggg tgattttatt acgatacaaa atcacgtatt atatactaac | 5820 |
| ccactaactg gcgctataac gacaggtatg caacaaattg gtgacaagat ttttgtcttt | 5880 |
| gacaatacgg gcaacatgtt gaccaatcaa tactatcaaa cactgatgg ccaatggtta | 5940 |
| catttaagca ctcaaggtcc agcagacact ggtttggtaa acattaatgg taatttgaaa | 6000 |
| tatttccaag ctaatggtcg gcaagtgaaa ggtcaatttg tgactgatcc tatcacgaac | 6060 |
| gtgagttatt atatgaatgc cactgatggt tcggcagtat ttaatgacta ctttacctat | 6120 |
| caaggccaat ggtatttaac ggatagtaat tatcaactcg tcaaaggatt taaagttgtt | 6180 |
| aataataagc tacaacattt tgatgaaata acaggcgtac aaactaaatc agctcatatc | 6240 |
| atcgttaata atcgaacata cattttcgat gaccaaggtt actttgtctc agtcgcttaa | 6300 |

<210> SEQ ID NO 2
<211> LENGTH: 6291
<212> TYPE: DNA
<213> ORGANISM: Artificial Sequence
<220> FEATURE:
<223> OTHER INFORMATION: Hybrid gene of dsrB and dex2

<400> SEQUENCE: 2

| | |
|---|---|
| atgctgtcta tgaccgctac ttcacaaaat gttaatgcag atagcacaaa cacagtgacg | 60 |
| gataagtcag ttactgtctc caataattcg aatacaacca atcaacacga tactgtcgtt | 120 |
| gacaaacaaa cgatacctgt caaaaatgac caaacaacac aacaaatcgc cgcaaatgcc | 180 |
| acccaagcag aaaaagtaaa agcatcagac acaacgactg atacgcaaaa gcaagctgaa | 240 |
| acggcaaaca cactaacaa ggattcgata gataatctca ccaagcagtt gccggctgtt | 300 |
| acaccaacag ctaatcaaaa aactggttat ctggaaaaag atggtaaatg gtactatgta | 360 |
| accagtgata cacacttgc taaggggttg actactgttg acaaccacaa gcagtatttt | 420 |
| gacaacaatg gcgtgcaggc aaaaggccaa ttcgttaccg ataacagtaa aacatactat | 480 |
| ctcgatccta actccggtaa cgcagtaacc gggatacaac aaattggctc acaaacatta | 540 |
| gccttcaatg acaacggtga acaagttttt gctgatttct atacagcgcc agatggcaaa | 600 |
| acttattatt ttgacgataa aggacaagca actattggtc taaaggccat taatgggcac | 660 |
| aattattact tcgatagttt gggacaacta aaaaaaggat ttaccggtgt cattgacggt | 720 |
| caagtacgct attttgatca agaatcagga caagaggtat caacaaccga ctcacaaatc | 780 |
| aaagaaggtt taacttctca gacaacagac tatacagcac ataatgccgt tcacagcacc | 840 |
| gatagcgctg atttcgacaa ttttaatggt tatttgaccg cttcttcatg gtatcgccct | 900 |
| aaagatgttt taagaaatgg tcaacactgg gaagcaacaa cagctaatga cttccggccc | 960 |
| attgtgtcag tttggtggcc tagcaagcaa acacaagtaa attacctaaa ctacatgtct | 1020 |
| caaatgggac tcattgacaa tcgtcagatg ttctcgctaa aagacaatca agccatgttg | 1080 |
| aatattgctt gcacaacagt ccaacaagca attgaaacaa aaatcggtgt ggctaatagt | 1140 |
| acagcatggc ttaaaacagc cattgatgat ttcattcgta cacagccaca atggaacatg | 1200 |
| tcgagtgaag atcccaaaaa tgatcattta caaacggcg ctttgacttt cgtcaacagt | 1260 |
| ccattgacac cagatactaa ctctaatttc agactattaa atcgcacacc aacaaaccag | 1320 |
| acaggtgtgc caaaatatac aattgatcaa tctaagggtg gttttgaact cttactcgct | 1380 |

```
aatgatgtag acaactctaa tcctgttgtg caagctgagc agttaaattg gttacactat    1440
ttgatgaatt ttggtagcat tacagcaaac gattctgctg ctaattttga tgggatacgt    1500
gtcgatgctg tcgataatgt tgacgctgat ttactccaga ttgcagcaga ttatttcaaa    1560
gctgcttatg gtgttgataa aaatgacgca acagcaaatc aacatctttc aattcttgaa    1620
gattggagcc ataacgaccc tgaatacgtg aaggattttg gtaataatca actcacaatg    1680
gatgattaca tgcataccca gttaatctgg tccttgacta agatatgcg tatgcgtggt    1740 accatgcaac gcttcatgga ctattacctc gtcaatcgca atcacgatag taccgaaaac    1800
actgccattc caaattacag ctttgttcgc gcacacgata gtgaagtaca acagtcatt    1860 gctcaaatta tttctgagtt acatcccgac gtaaaaaata gtttggcacc aacagcagac    1920
cagctagccg aagcctttaa aatttataat aacgatgaaa acaggcgga taagaaatat    1980 acacaataca acatgcctag cgcctatgcg atgctgttaa ctaataaaga tacagtaccg    2040
cgcgtttatt atggtgattt atacaccgat gatggtcaat atatggcaaa taagtcccct    2100
tattttgatg ccatcaacgg cttgctaaag tcacgtatca aatatgttgc tggtggtcag    2160
tcaatggctg ttgatcaaaa cgatatcctg acaaatgttc gttatggtaa aggtgccatg    2220
agtgtgacag atagcggtaa tgcagacaca cgaacacaag gtattggtgt gattgtcagt    2280 aataagaaa atctggcctt aaaatcaggc gacacggtga cattacacat gggtgccgct    2340
cacaaaaatc aagcattcag attattatta gggacaactg ctgacaattt gtcttattat    2400
gataatgaca acgcccagt aaagtacacc aatgatcagg gcgatttaat ttttgataat    2460
actgaaatct atggtgtccg taacccgcaa gtctctggct tcttagctgt ttgggtgcct    2520 gttgggctg acagccatca agacgcgcgt actttgtctg acgacacagc ccatcatgat    2580
ggcaaaacct tccactcaaa tgctgcttta gattctcagg ttatttacga aggttttttca    2640 aatttccaag cttttgccac aaacactgaa gactatacaa atgctgtcat tgcaaaaaat    2700
ggtcagttat tcaaagattg gggtatcaca agtttccagt tggcaccaca atatcgttca    2760
agcaccgata ccagtttctt agattcaatt atccaaaatg gttatgcctt tacagatcgt    2820
tatgatttag gctacggtac accaacaaaa tatggcacag ttgaccagtt acgcgatgcc    2880
atcaaggctc tgcacgcaaa tggcatccaa gcaatcgctg actgggtacc cgaccaaatt    2940
tataatttac cgggtcaaga attagcgacc gtcacccgaa caaactctta tggtgataaa    3000
gacactaact cagatattga tcagtcacta tatgtcatac aaagtcgtgg tggtggtaaa    3060
taccaagcac agtatggcgg tgccttctta tccgatatcc agaaaaaata tccagcactt    3120
ttcgaaacaa aacaaatttc tacagggcta cctatggatc ctagtcagaa ataacagaa    3180 tggtctggta aatactttaa tggctcaaat attcaaggca aaggggctgg ctatgtcttg    3240
aaagacagtg gtaccgatca atactataag gttacatcaa acaataataa tcgtgacttc    3300
ttgccaaaac aattaacaga tgacttatct gaaaccggat ttgtccgcga taacattggt    3360
atggtctatt acacactgag tggctatcta gctcgaaaca cctttataca agatgataat    3420
ggcaattatt attactttga tagcaccggc catctcgtta ctggcttcca gaatattaat    3480
aaccatcact atttcttcct accaaacggt attgaactcg ttcaatcttt cttacagaat    3540
gctgacggtt caacgattta ttttgaccaa aaagggcgtc aagtatttaa tcaatacatt    3600
actgaccaaa ccggtaccgc ctattacttc cagaatgatg gcacaatggt cacttctggc    3660
ttcactgaaa tcgatggtca taagcaatac ttctacaaga acggcacaca agtcaaaggg    3720
caatttgtat cagacactga tggtcacgtt ttctacttag aagctggtaa cggcaacgtg    3780
```

```
gcgacacaaa gatttgcaca aaatagtcaa ggtcagtggt tctatttggg taatgatggc   3840
attgccttga ctggtttgca aacaatcaat ggtgttcaaa attatttcta cgccgatggt   3900
catcaaagta agggtgattt tattacgata caaaatcacg tattatatac taacccacta   3960
actggcgcta taacgacagg tatgcaacaa attggtgaca agattttgt ctttgacaat   4020 acgggcaaca tgttgaccaa tcaatactat caaacactag atggccaatg gttacattta   4080
agcactcaag gtccagcaga cactggtttg gtaaacatta atggtaattt gaaatatttc   4140
caagctaatg gtcggcaagt gaaaggtcaa tttgtgactg atcctatcac gaacgtgagt   4200
tattatatga atgccactga tggttcggca gtatttaatg actactttac ctatcaaggc   4260
caatggtatt taacggatag taattatcaa ctcgtcaaag gatttaaagt tgttaataat   4320
aagctacaac attttgatga aataacaggc gtacaaacta aatcagctca tatcatcgtt   4380
aataatcgaa catacatttt cgatgaccaa ggttactttg tctcaagatc taagcattac   4440
ctccgtctat tggcctcagc atttgcgctg ctgctcctgc tgccggctgc cggccaggag   4500
ccagccgctg cgacagaaca gaccggtttc actgccaccg acccggcct tcggacctgg   4560 tggcacaaca actacgaata caacccaacc tcacccaccc agaacggcac agtccgccgg   4620 tcatccttt acgaggtgca agtagccaca gcaacggcac caggaacgcg ctacgactcc   4680
ttcgcctaca tgagcattcc ccgcagcgga aaggggaaga ccggctacac ggagccggac   4740
ggagcagagt tctcttcgtc agcgaacctc tcaatgagct ggtccagctt tgagtactca   4800
acggacgtct gggtggacgt caaactcacg acaggccaaa caatcacgtc tgtggatcag   4860
gtaacgatcc ggcccagcaa gtacaccttc gagaaagagc tggtgaaccc cagcaccatc   4920
cgggtcaaag tcccctactc gtcgacgggc taccggctct cagtggaatt cgcgcccag   4980 ctcttcactg catacaacga catgtccgga acggcggggg tgttgactga aaccggtggc   5040
ggggatcacc cgccatcca taccgaacca cggaattcca tgatgatctt cgccgagccg   5100
accctgggcg gcggcgaggc ggagcggttg attcccacct ccgcatccgg agctatcaac   5160
tatccgcagg aaggcctggt cgacaacctg gggtcggtca ccgaggagat catctacttc   5220
cggcccggga cgtattacat gggatcggac caccgggcct cgatgccgcc caacgtcaaa   5280
tggatctacc tggctcccgg ggcgtatgtc aaaggtgcct tctacttccc caactcgacg   5340
cagggcgtct acaaggtcac tggccgcggc gtgctctccg gcgaacagta cgtctatgaa   5400
gccgatacaa ccaccagcgg gtacacgcat tcaaccggcg ctaattgcca caacacctgc   5460
gtgaagatgc tggaattcac gtcttcatcg accatgcagc agtacttgga cgtggaggga   5520
atcaccatca gcgaacctcc ctaccactcc tttgtcattt acgggccgca aaacgcctat   5580
gagatggaaa tgcgggtgga taactacaag caggtgggca gctggtactg gcagaccgac   5640
gggatggaac tctacgaggg cggcggatg aacaacacct tttccactc caatgatgac   5700 gtcctgaagc tctaccacag caacgtgacg gtggataaca cggtgatctg gaagaacgag   5760
aacggtccgg tcatccagtg ggggttgggcg ccgtacaaca ttgacaatgt ggtcgtcacc   5820
aacacagacg tcatccacaa ccgcatgtat tggaaggacg tcaaatacaa cacctgcatc   5880
atcaactcgt cctcccacta cgcggacatg ggctcctcca ccacggcgaa ccccgccacc   5940
acgatcagga atttccggct ggagaacatt actgtcgaag gaatgaccaa ctgcgccctc   6000
aggatctatg cgcttttccaa caccgagaac atccacatca agaacctgaa tatcggaagc   6060
tggaacgggt tggaccacac gtcccaggtg agccacctga agcgctattc agacactgcc   6120
aacaacaagg tctggctggg caacgagact gtcgacagca gaggcatcaa gctcgagaac   6180
```

```
tacaccgtcg gcggggccag gatcgacaaa accacgacca actggagcga taaccaggcg    6240
ggccgtctcg gcttcgacgg cgaaaactgg gataactgga acgcgtggtg a             6291
```

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3

```
attttatctc gagttatgct gtctatga                                         28
```

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4

```
ggcttttttt agttaagatc ttgagaca                                         28
```

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5

```
gatcgatgga tcagatctaa gcattac                                          27
```

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6

```
atcaagcttc gaattccatg gtaccc                                           26
```

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7

```
attttatctc gagttatgct gtctatga                                         28
```

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8

```
ggcttttttt agttaagatc ttgagaca                                         28
```

<210> SEQ ID NO 9
<211> LENGTH: 27

-continued

```
<212> TYPE: DNA
<213> ORGANISM: Artificial Sequence
<220> FEATURE:
<223> OTHER INFORMATION: Primer

<400> SEQUENCE: 9
gatcgatgga tcagatctaa gcattac                                    27

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
atcaagcttc gaattccatg gta                                        23
```